(12) United States Patent
Cho et al.

(10) Patent No.: US 12,239,979 B2
(45) Date of Patent: Mar. 4, 2025

(54) GENOME EXTRACTION DEVICE OF DUAL CHAMBER STRUCTURE IN WHICH OUTER CHAMBER AND INNER CHAMBER ARE COMBINED WITH EACH OTHER

(71) Applicant: SD BIOSENSOR, INC., Suwon-si (KR)

(72) Inventors: Young-Shik Cho, Yongin-si (KR); Hae-Joon Park, Seongnam-si (KR); Sunyoung Lee, Suwon-si (KR); Kwanhun Lim, Daejeon (KR); In-Ae Kim, Suwon-si (KR); Dong-Hun Kim, Suwon-si (KR)

(73) Assignee: SD BIOSENSOR, INC., Suwon-si (KR)

(*) Notice: Subject to any disclaimer, the term of this patent is extended or adjusted under 35 U.S.C. 154(b) by 709 days.

(21) Appl. No.: 17/455,554

(22) Filed: Nov. 18, 2021

(65) Prior Publication Data

US 2022/0410150 A1  Dec. 29, 2022

(30) Foreign Application Priority Data

Jun. 29, 2021 (KR) .......... 10-2021-0084992

(51) Int. Cl.
*B01L 3/00* (2006.01)
*C12N 15/10* (2006.01)

(52) U.S. Cl.
CPC .... *B01L 3/502715* (2013.01); *C12N 15/1017* (2013.01); *B01L 2200/027* (2013.01); *B01L 2200/0689* (2013.01)

(58) Field of Classification Search
CPC ......... B01L 3/502715; B01L 2200/027; B01L 2200/0689; B01L 2200/141; B01L 2300/0672; B01L 3/565; B01L 2200/021; B01L 2200/026; B01L 2300/0609; B01L 9/50; B01L 2200/028; B01L 2300/042; B01L 2300/044; B01L 2300/0854; B01L 2400/0478; B01L 2400/0644; B01L 3/527; B01L 3/502; C12N 15/1017
USPC ...................................... 435/287.2
See application file for complete search history.

(56) References Cited

U.S. PATENT DOCUMENTS

2014/0205514 A1*  7/2014  Hwang ............... B01L 3/508
                                                        422/533
2019/0338346 A1   11/2019  Connolly et al.
2021/0031181 A1*   2/2021  Yanez ............... B01L 3/5025

FOREIGN PATENT DOCUMENTS

| KR | 20180098089 | * | 9/2018 |
| KR | 10-1989920 | B1 | 6/2019 |
| KR | 10-2065649 | B1 | 1/2020 |
| KR | 10-2065650 | B1 | 2/2020 |
| KR | 10-2076220 | B1 | 2/2020 |
| KR | 10-2020-0056268 | A | 5/2020 |

* cited by examiner

Primary Examiner — Jill A Warden
Assistant Examiner — Jacqueline Brazin
(74) Attorney, Agent, or Firm — Harvest IP Law, LLP

(57) ABSTRACT

Provided is a genome extraction device to which a dual chamber structure of an outer chamber and an inner chamber is applied, more particularly a genome extraction device to which the above-described dual chamber structure is applied so that the genome extraction device can be stored stably for a long time without the risk of reagent leakage.

12 Claims, 22 Drawing Sheets

GENOME EXTRACTION DEVICE OF DUAL CHAMBER STRUCTURE IN WHICH OUTER CHAMBER AND INNER CHAMBER ARE COMBINED WITH EACH OTHER

CROSS-REFERENCE TO RELATED PATENT APPLICATION

This application claims the benefit of Korean Patent Application Serial No. 10-2021-0084992 filed on Jun. 29, 2021 in the Korean Intellectual Property Office; the disclosure of which is incorporated herein in its entirety by reference.

BACKGROUND

1. Field

The present disclosure relates to a genome extraction device of a dual chamber structure in which an outer chamber and an inner chamber are combined with each other.

2. Description of the Related Art

In modern times, as biotechnology has developed, the causes of diseases at a genetic level can be interpreted. Accordingly, there is an increasing demand for manipulation and biochemical analysis of biological specimens for curing or preventing human diseases.

In addition, technology for extracting and analyzing nucleic acids from biological specimens or specimens containing cells is required in various fields such as new drug development, pre-test for viral or bacterial infection, and forensics in addition to disease diagnosis.

Genome extraction devices according to the related art require a separate device for each treatment process (concentration, purification), and require a long time because the genome extraction devices need to be moved to another device after one treatment process is completed.

In order to solve the conventional problem of low detection efficiency due to such a long treatment process, Korean Registered Patent No. 10-1989920 by the present applicant has been developed and used.

In the above literature, a buffer is directly dispensed and stored inside a buffer chamber, but there is a problem in that micro-leakage occurs through various layer structures under the buffer chamber during long-term storage and adversely affects extraction performance.

In addition, a pad disposed between an upper body and a base plate is made of a rubber material, and as the pad is compressed between the upper body and the base plate, the diameter of holes formed through the pad decreases, so that there is a problem in that an extract having a capacity different from a product design intention moves to an amplification module.

In addition, there is a problem in that a sealing member sealing the buffer chamber is perforated by a protrusion member due to vibration generated during production and distribution of a product, such that a reagent stored in the buffer chamber is leaked and contaminated.

PRIOR-ART DOCUMENTS

Patent Document

Korean Registered Patent No. 10-1989920 (Jun. 11, 2019)
Korean Registered Patent No. 10-2065649 (Jan. 7, 2020)
Korean Registered Patent No. 10-2065650 (Jan. 7, 2020)
Korean Registered Patent No. 10-2076220 (Feb. 5, 2020)

SUMMARY

The present disclosure provides a genome extraction device in which an inner chamber containing reagents required for genome extraction is provided separately from an outer chamber and which solves a problem where a reagent contained in a single chamber in a genome extraction device according to the related art leaks out to the outside, because upper and lower portions of the inner chamber are sealed.

The present disclosure also provides a genome extraction device including a safety clip for preventing a sealing member sealing upper and lower openings of an inner chamber from being perforated by protrusion members formed in a cover and an outer chamber, because the inner chamber moves up and down due to vibration generated during a production and distribution process of a product.

The present disclosure also provides a genome extraction device that solves a problem of cross-contamination between reagents due to capillary action occurring through a space between dual chambers through a unique inner chamber design (lower inner chamber).

The present disclosure also provides a genome extraction device that solves a problem where reagents leak out to the outside, through a unique inner chamber design (upper inner chamber) in a structure for preventing capillary action.

The present disclosure also provides a genome extraction device in which, by using the configuration of a first protrusion member formed on a bottom surface of the outer chamber, the sealing member can be torn with a small force, the perforated portion is expanded and the reagent contained in the inner chamber is smoothly discharged to the outside.

The present disclosure also provides a genome extraction device in which an inclined portion is formed around a discharge hole through which reagents are discharged, so that the reagents are smoothly discharged through the discharge hole.

The present disclosure also provides a genome extraction device in which a dual-structured flow cover-pad is arranged between an outer chamber and a base plate, the convenience of manufacturing is improved, and the problem of unintentional narrowing of a flow path is solved compared to a genome extraction device according to the related art in which only one pad is disposed.

The present disclosure also provides a genome extraction device in which firm coupling between a base plate, a flow cover, a pad, and an outer chamber is achieved so that sealed flow paths are formed without a phenomenon where reagents do not leak out from the middle during the movement of reagents.

The present disclosure also provides a genome extraction device in which a bead chamber, in which beads required for genome extraction and amplification are accommodated, also has a dual chamber structure of an outer chamber and the bead chamber, so that the performance of the beads vulnerable to moisture can be maintained for a long time.

The present disclosure also provides a genome extraction device in which, even when a bead chamber is opened, the performance of beads is maintained by a dehumidification unit positioned above the bead chamber.

The present disclosure also provides a genome extraction device in which, as a pre-treated extract is introduced, air remaining inside an accommodating portion may be easily discharged so that an amplification module in which an extract having a sufficient capacity can be introduced, which can be applied to the genome extraction device.

The present disclosure also provides a genome extraction device in which an amplification module has a plurality of accommodating portions, primers and probes for amplifying different genomes are stored in each of the plurality of accommodating portions, and various types of diseases can be diagnosed through single genome extraction.

The present disclosure also provides a genome extraction device in which the length, thickness, and patterns of a gas moving passage and an extract moving passage are provided differently depending on the location of the connected accommodating portion so that the extract or amplification product injected into the accommodating portion can be prevented from being mixed.

The present disclosure also provides a genome extraction method using the above-described genome extraction device.

According to an aspect of the present disclosure, an extraction device includes: an outer chamber partitioned into a plurality of first spaces by an outer chamber partition wall; and an inner chamber coupled to the outer chamber through upper openings of the plurality of first spaces and partitioned into a plurality of second spaces by an inner chamber partition wall, wherein the inner chamber includes: an upper inner chamber in close contact with an inner wall of the plurality of first spaces of the outer chamber; and a lower inner chamber connected to the upper inner chamber and including a curved portion toward a radially inner side from the upper inner chamber so as to be spaced apart from the inner wall of the plurality of first spaces.

Upper openings of the plurality of second spaces of the inner chamber may be covered by a first sealing member, and the genome extraction device may further include a cover configured to cover the upper openings of the plurality of first spaces of the outer chamber and having a first protrusion member formed on a bottom surface of the cover and configured to tear the first sealing member.

Lower openings of the plurality of second spaces of the inner chamber may be covered by a second sealing member, and a second protrusion member configured to tear the second sealing member may be formed on a bottom surface of the plurality of first spaces of the outer chamber.

The first sealing member and the second sealing member may be films.

The first protrusion member may include: protrusions protruding from the bottom surface of the plurality of first spaces by a first height; and wing portions extending from the protrusions and protruding from the bottom surface by a second height that is lower than the first height.

A coupling hook may be formed on an outer surface of the upper inner chamber, and an insertion space to which the coupling hook is coupled may be recessed in the inner wall of the outer chamber.

A locking protrusion may protrude from the inner wall of the outer chamber toward a radially inner side on an upper side of the insertion space, and when the cover is coupled to the outer chamber, the coupling hook may be inserted into the insertion space by passing through the locking protrusion.

When the cover is coupled to the outer chamber, the first protrusion member may be configured to tear the first sealing member and the second protrusion member may be configured to tear the second sealing member so that a fluid accommodated in the plurality of second spaces of the inner chamber is introduced into the plurality of first spaces of the outer chamber.

First discharge holes may be formed through the bottom surface of a part of the plurality of first spaces along a circumferential direction while being spaced apart from a central portion of the outer chamber by a first distance, and second discharge holes may be formed through the bottom surface of the other part of the plurality of first spaces along the circumferential direction while being spaced apart from the central portion of the outer chamber by a second distance that is greater than the first distance.

The genome extraction device may further include a piston, wherein the piston includes: an upper piston having an open upper portion, a fluid accommodating portion in which fluids discharged through the first discharge holes and the second discharge holes are accommodated and which is formed therein, and holes formed in a lower portion of the upper piston to be aligned with the first discharge holes or the second discharge holes; a close contact portion installed to be lifted or lowered inside the fluid accommodating portion; and a lower piston coupled to the upper piston and having a liquid port and a filter port formed on a lower portion of the lower piston.

The genome extraction device may further include a driving unit coupled to the lower piston by passing through a base plate, wherein the lower piston rotates by driving of the driving unit so that the liquid port or the filter port communicates with one of the plurality of first spaces.

When the close contact portion is lifted inside the fluid accommodating portion, fluids accommodated in any one of the plurality of first spaces may be inhaled into the fluid accommodating portion through the liquid port, and when the close contact portion is lowered inside the fluid accommodating portion, fluids in the fluid accommodating portion may be discharged into any one of the plurality of first spaces through the filter port.

The genome extraction device may further include an amplification module, wherein the amplification module includes: an injection port coupled to the genome extraction device; an accommodating portion that is a space in which fluids discharged through the injection port are accommodated; a gas moving passage formed on one surface of the amplification module and configured to connect the injection port to the accommodating portion; and an extract moving passage formed on an opposite surface to the one surface and configured to connect the injection port to the accommodating portion.

BRIEF DESCRIPTION OF THE DRAWINGS

The above and other features and advantages of the present disclosure will become more apparent by describing in detail exemplary embodiments thereof with reference to the attached drawings in which.

DETAILED DESCRIPTION

In some cases, well-known structures and devices may be omitted or shown in a block diagram form focusing on core functions of each structure and device in order to avoid obscuring the concept of the present disclosure.

Throughout the specification, when a portion is said to be "comprising or including" a certain component, it does not exclude other components unless otherwise stated, meaning that other components may be further included. In addition, terms such as " . . . unit", " . . . group", and "module" described in the specification mean a unit that processes at least one function or operation, which may be implemented as hardware or software or a combination of hardware and software. Also, "a or an", "one", "the", and like related terms are used differently herein in the context of describing the disclosure (especially in the context of the following claims). Unless indicated or clearly contradicted by context, such terms may be used in a sense including both the singular and the plural.

In describing the embodiments of the present disclosure, if it is determined that a detailed description of a well-known function or configuration may unnecessarily obscure the gist of the present disclosure, a detailed description thereof will be omitted. In addition, the terms to be described later are terms defined in consideration of functions in an embodiment of the present disclosure, which may vary according to intentions or customs of users and operators. Therefore, the definition should be made based on the content throughout this specification.

Hereinafter, the present disclosure will be described in detail with reference to the accompanying drawings.

Figure 1:
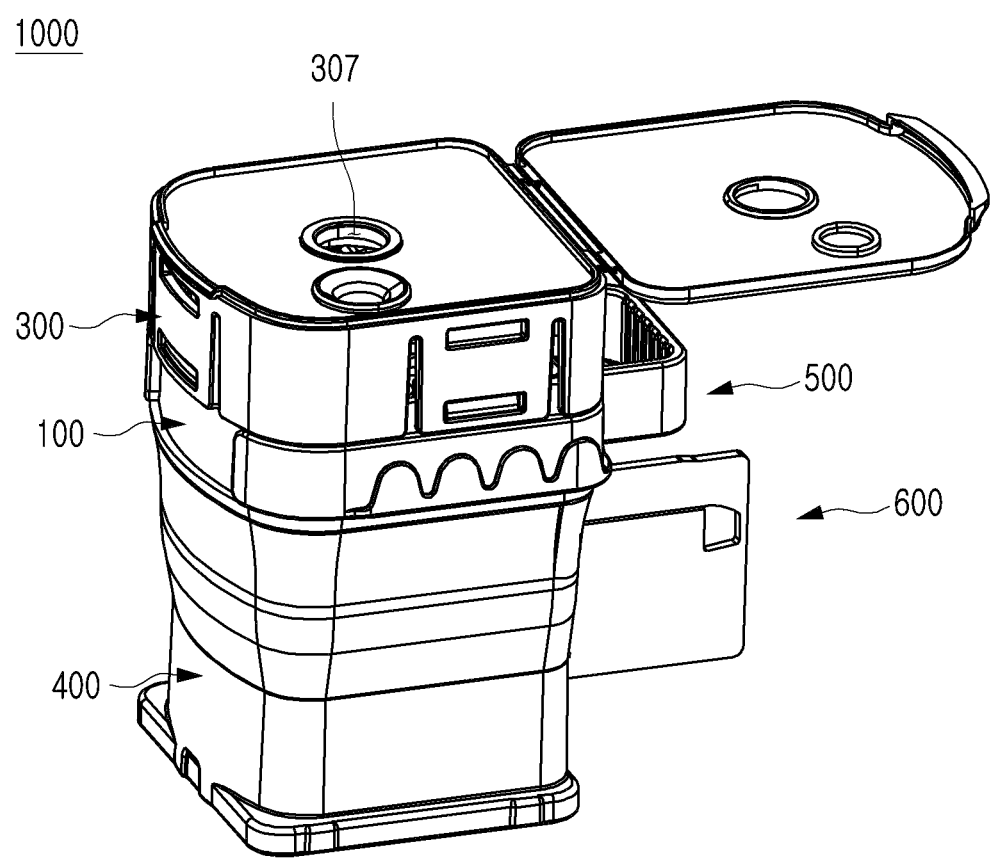
FIG. 1 is a perspective view showing the overall appearance of a genome extraction device according to an embodiment of the present disclosure.
Figure 2:
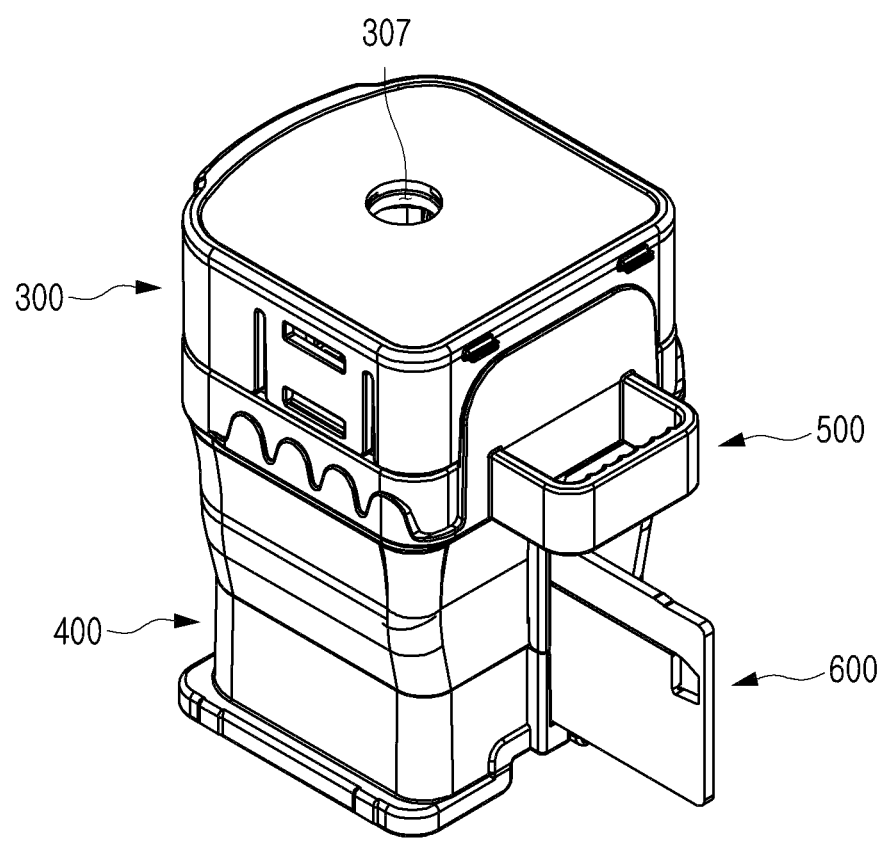
FIG. 2 is a perspective view showing the genome extraction device of FIG. 1 viewed from another side.

Referring to FIGS. 1 and 2, a genome extraction device 1000 according to an embodiment of the present disclosure includes an outer chamber 100, an inner chamber 200, a cover 300, a base plate 400, a safety clip 500, an amplification module 600, a piston 700, a driving unit 800, ad a bead chamber 900.

The outer chamber 100 is partitioned into a plurality of first spaces 101, 102, 103, 104, 105, 106, and 107 by an outer chamber partition wall. That is, the plurality of first spaces 101, 102, 103, 104, 105, 106, and 107 may be mutually independent spaces.

Each of the plurality of first spaces 101, 102, 103, 104, 105, 106, and 107 may have an open upper portion and a closed lower portion. On the other hand, first discharge holes 121, 122, 123, 124, and 125 are formed through bottom surfaces of the plurality of first spaces 101, 102, 103, 104, and 105 along a circumferential direction while being spaced apart from the central portion of the outer chamber 100 by a first distance, and second discharge holes 126 and 127 are formed through bottom surfaces of the remaining first spaces 106 and 107 along the circumferential direction while being spaced apart from the central portion of the outer chamber 100 by a second distance. In addition, discharge holes 128 and 129 that communicate with the amplification module 600 are formed through a bottom surface of a space between the first spaces 106 and 107. Here, the first distance may be shorter than the second distance, but in another embodiment, the first distance may be longer than the second distance.

Reagents stored in the inner chamber 200 to be described later are put into the plurality of first spaces 101, 102, 103, 104, and 105, and beads stored in the bead chamber 900 are put into the remaining first spaces 106 and 107.

A piston insertion portion 108 into which the piston 700 is inserted is formed through the center of the plurality of first spaces 101, 102, 103, 104, 105, 106, and 107 in a vertical direction. The piston 700 is inserted into the piston insertion portion 108, and a driving unit (not shown) of a diagnostic device is combined with the piston 700 to elevate the piston 700 so that the reagents (fluids) of the first spaces 101, 102, 103, 104, 105, 106, and 107 may enter and exit a fluid accommodating portion 701 inside the piston 700. More specific details will be described later.

Figure 4:
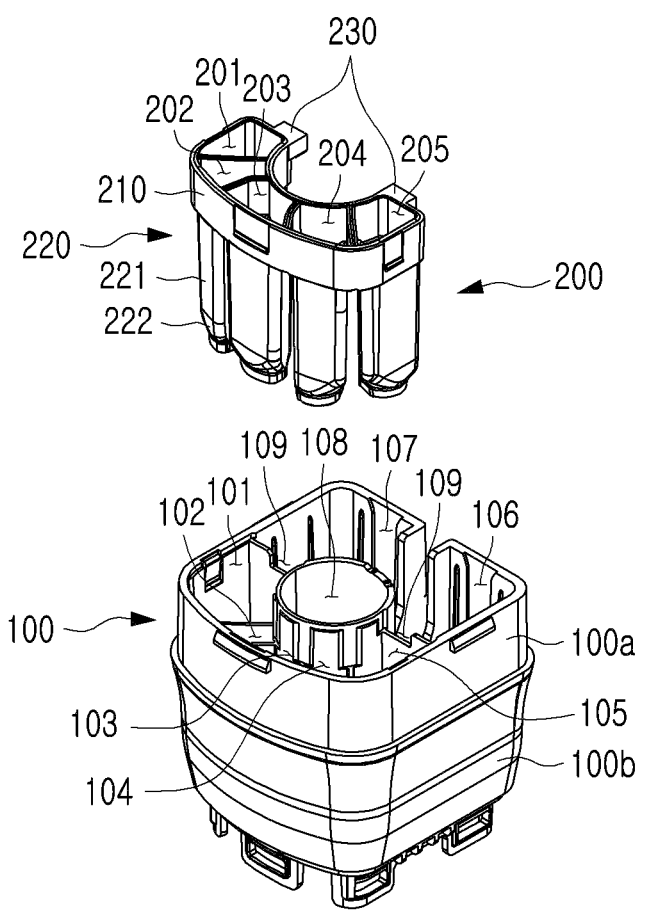
FIG. 4 is a view for describing a combination relationship between an outer chamber and an inner chamber.

Referring to FIG. 4, an outer surface upper portion 100*a* of the outer chamber 100 is connected to the upper portion of an outer surface lower portion 100*b*, and is recessed toward the central portion of the outer chamber 100. The safety clip 500 is combined with the outer surface upper portion 100*a* of the outer chamber 100, and a boundary between the outer surface upper surface 100*a* and the outer surface lower surface 100*b* serves as a step of the safety clip 500, so that the safety clip 500 is combined with the outer surface upper portion 100*a* and then the combination position thereof may be maintained. The safety clip 500 includes an outer chamber coupling portion 510 having a length for at least partially surrounding a perimeter of the outer surface upper portion 100*a* of the outer chamber 100 and extending, and a handle 520 formed on one side of the outer chamber coupling portion 510.

As the safety clip 500 is coupled to the outer chamber 100, the cover 300 presses the inner chamber 200 coupled to the outer chamber 100 to prevent upper and lower openings of the inner chamber 200 from being opened. A user is able to start an extraction process after removing the safety clip 500 from the outer chamber 100 by gripping the handle 520. In other words, when the safety clip 500 is coupled to the outer chamber 100, the reagent of the inner chamber 200 is not introduced into the outer chamber 100, and only when the safety clip 500 is removed from the outer chamber 100, the reagent of the inner chamber 200 may be introduced into the outer chamber 100.

Figure 5:
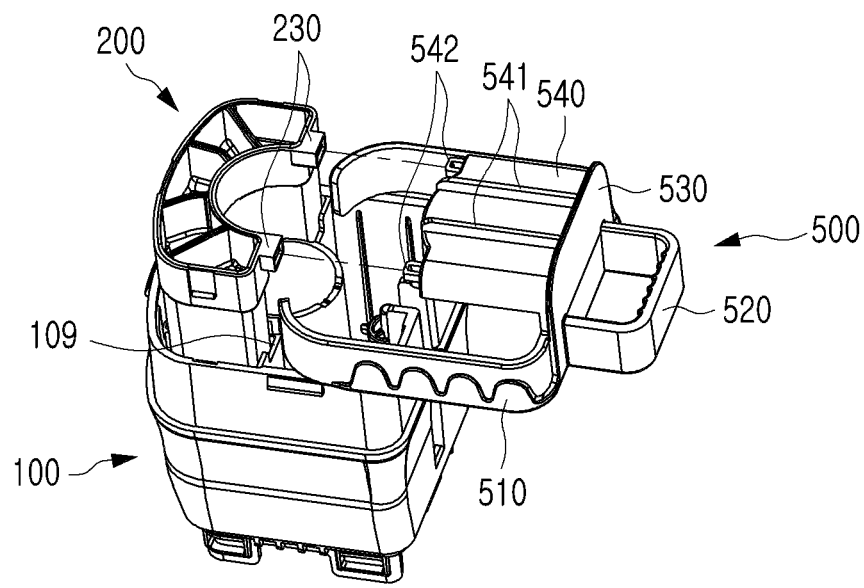
FIG. 5 is a view for describing a combination relationship between the inner chamber and a safety clip.
Figure 6:
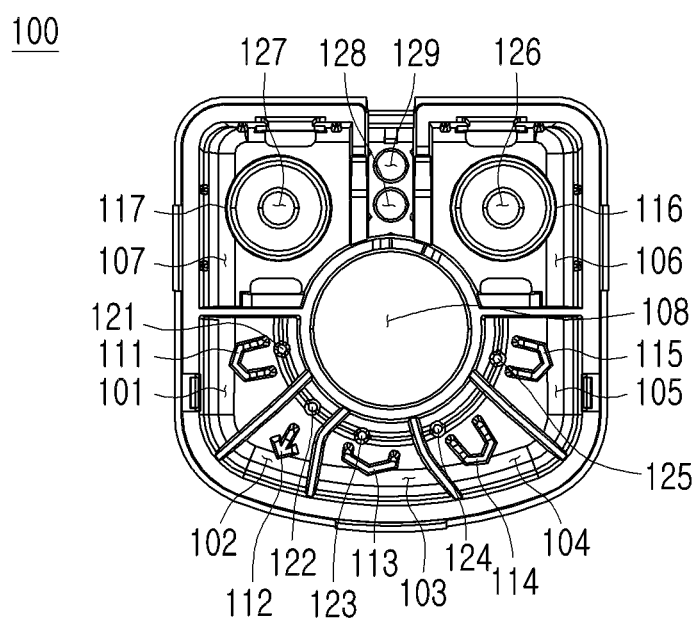
FIG. 6 is a plan view of the outer chamber.

The configuration of the safety clip 500 will be described in more detail with reference to FIGS. 3 through 5.

The safety clip 500 includes an outer chamber coupling portion 510, a handle 520, an upper extension portion 530, and a side extension portion 540.

The outer chamber coupling portion 510 is coupled to the outer chamber 100 while at least partially surrounding the perimeter of the outer surface (specifically the outer surface upper portion 100a) of the outer chamber 100. More specifically, the outer chamber coupling portion 510 is coupled to the outer chamber 100 so as to surround four outer surfaces of the outer chamber 100, and the extended ends of the outer chamber coupling portion 510 may be configured to be spaced apart from each other. As shown in FIG. 1, when the safety clip 500 is coupled to the outer chamber 100, the extended end of the outer chamber coupling portion 510 is caught on the outer surface of any one of the outer chamber 100, so that the safety clip 500 can be separated from the outer chamber 100 only when the user grips the safety clip 500 and applies an external force in one direction.

The handle 520 is a portion extending outwardly from the outer chamber coupling portion 510, and is a portion gripped by the user to separate the safety clip 500 from the outer chamber 100.

The upper extension portion 530 extends upwardly from one side of the outer chamber coupling portion 510, and the side extension portion 540 extends from the upper extension portion 530 toward the center of the outer chamber 100.

In the safety clip 500 according to the embodiment of the present disclosure, a cover support member 541 protrudes from the upper surface of the side extension portion 540, and an inner chamber coupling portion 542 protrudes from the extended end of the side extension portion 540.

The cover support member 541 serves to prevent protrusion members 311, 312, 313, 314, 315, 316, and 317 formed on the bottom surface of the cover 300 from tearing (perforating) a first sealing member S1 for sealing upper openings of a plurality of second spaces 201, 202, 203, 204, and 205 of the inner chamber 200 and a third sealing member S3 for sealing the upper opening of the bead chamber 900.

Figure 15:
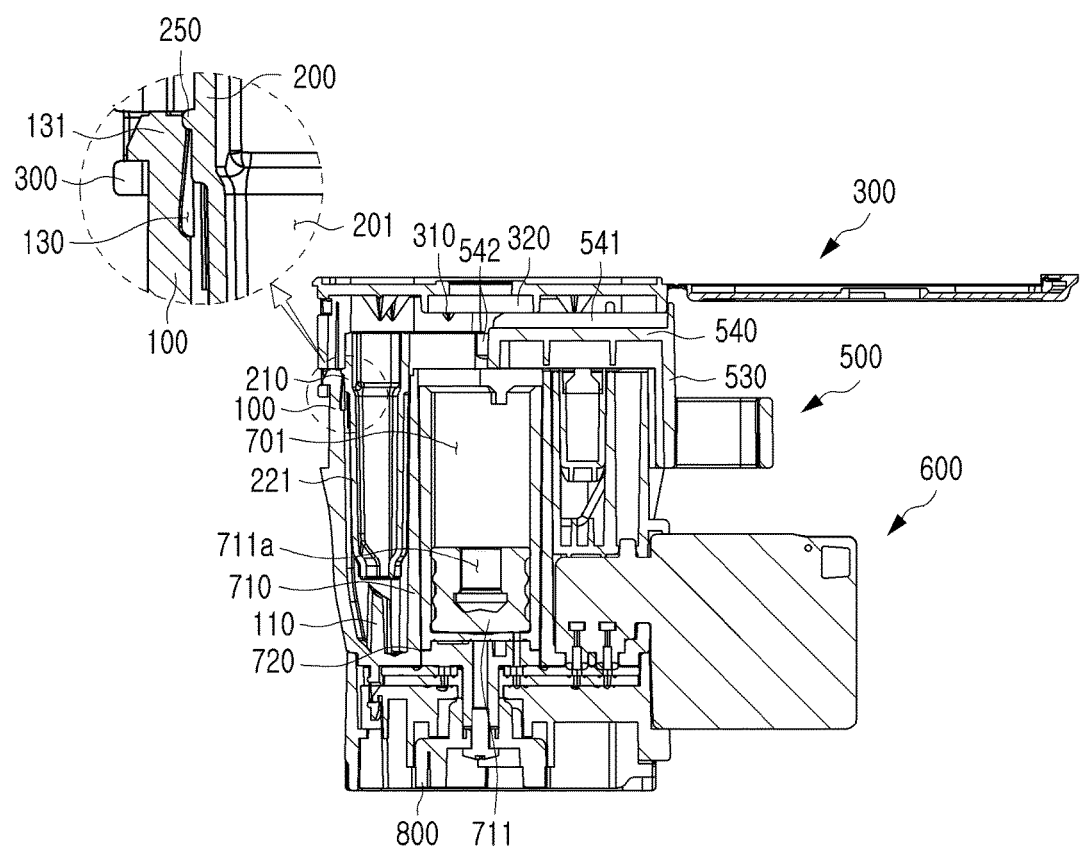
FIG. 15 is a cross-sectional view for specifically describing a genome extraction device according to an embodiment of the present disclosure.
Figure 16:
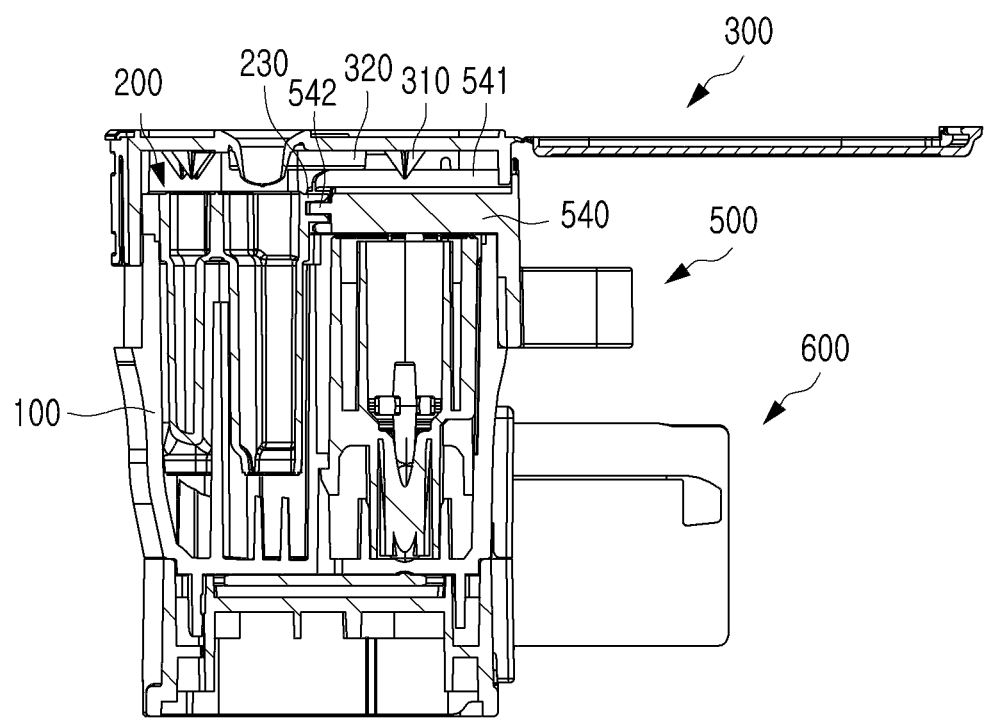
FIG. 16 is another cross-sectional view for specifically describing a genome extraction device according to an embodiment of the present disclosure.

As the cover support member 541 protrudes upwardly from the upper surface of the side extension portion 540, as shown in FIG. 15, when the safety clip 500 is coupled to the outer chamber 100 and the inner chamber 200, contact is blocked between the protrusion members 311, 312, 313, 314, 315, 316, and 317, the first sealing member S1, and the third sealing member S3. Therefore, when the safety clip 500 is coupled to the outer chamber 100 and the inner chamber 200, the inner chamber 200 and the bead chamber 900 are prevented from being perforated, so that a phenomenon in which the reagent accommodated in the inner chamber 200 and beads accommodated in the bead chamber 900 leak out through the outer chamber 100 can be prevented.

The inner chamber coupling portion 542 is a portion coupled to a fixing portion 230 of the inner chamber 200 when the safety clip 500 is coupled to the outer chamber 100. When the inner chamber coupling portion 542 is coupled to the fixing portion 230, the bottom surface of the inner chamber 200 is located at a position spaced a predetermined distance from the bottom surface of the outer chamber 100. Thus, a second sealing member S2 for sealing lower openings of the plurality of second spaces 201, 202, 203, 204, and 205 can be prevented from being torn by the protrusion members 111, 112, 113, 114, and 115 formed on the bottom surface of the outer chamber 100 (see FIG. 15).

In the accompanying drawings, the inner chamber coupling portion 542 is shown in the form of a coupling protrusion, and the fixing portion 230 is shown in the form of a coupling groove coupled to the coupling protrusion. However, in another embodiment, the inner chamber coupling portion 542 may be provided in the form of a coupling groove, and the fixing portion 230 may be provided in the form of a coupling protrusion coupled to the coupling groove.

A seating portion 109 providing a space in which the fixing portion 230 of the inner chamber 200 is seated, is recessed in the outer chamber 100 (more specifically, an outer chamber partition wall). The inner chamber 200 is fixed at a position spaced a predetermined distance from the bottom surface of the outer chamber 100 through a coupling structure with the safety clip 100. However, as the fixing portion 230 of the inner chamber 200 is seated on and supported by the seating portion 109, a fixing force can be further increased.

Figure 7:
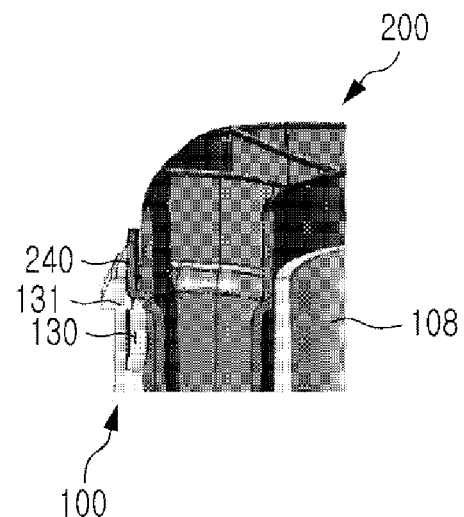
FIG. 7 is a cross-sectional view for describing a combination relationship between the inner chamber and the outer chamber.
Figure 8:
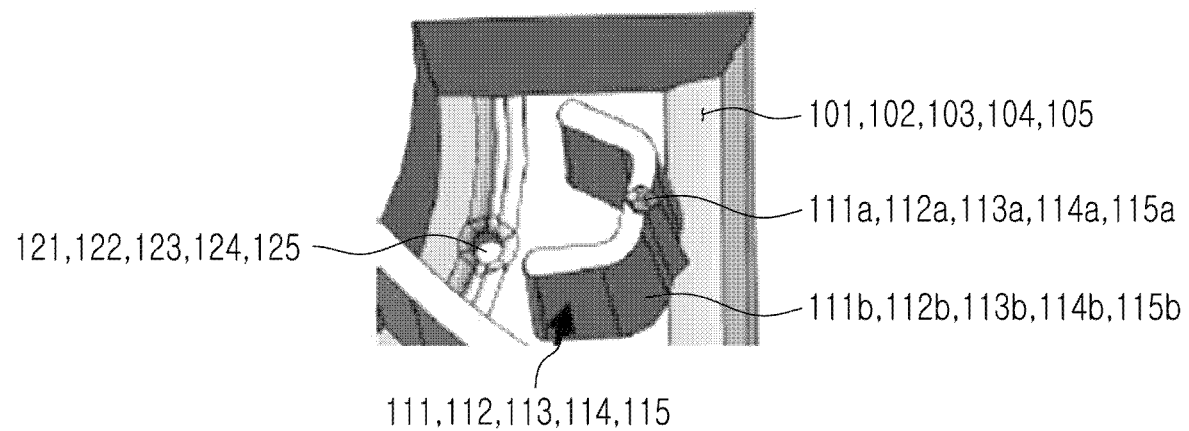
FIG. 8 is an enlarged view for describing a protrusion member formed on a bottom surface of the outer chamber.
Figure 9:
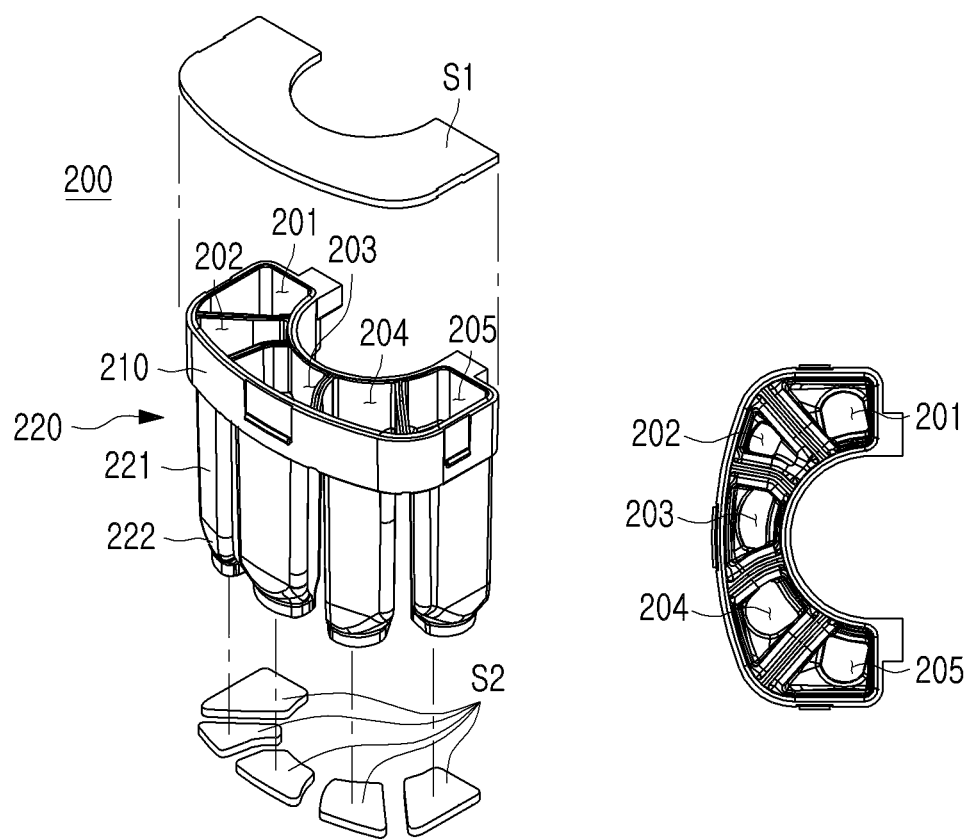
FIG. 9 is a view for describing the inner chamber in more detail.

Referring to FIG. 7, an insertion space 130 may be recessed on an upper side of an inner wall of the outer chamber 100, and a coupling hook 240 of the inner chamber 200 may be coupled to the insertion space 130. A stopper 131 protrudes toward the inside of the outer chamber 100 on the upper side of the insertion space 130. Therefore, when the inner chamber 200 is not pressed by the cover 300, the coupling hook 240 of the inner chamber 200 is located on the stopper 131. However, when the inner chamber 200 is pressed by the cover 300, the coupling hook 240 may be inserted into the insertion space 130 by passing through the stopper 131.

Referring to FIG. 15, an outer chamber-inner chamber coupling relationship according to another embodiment of the present disclosure will be described. In FIG. 7, instead of the coupling hook 240 formed in the inner chamber 200, a locking protrusion 250 protruding outwardly from the outer wall of the inner chamber 200 is provided, the locking protrusion 250 is caught by the stopper formed on the inner wall of the outer chamber 100, and the downward movement of the inner chamber 200 is partially restricted. When the safety clip 500 is removed from the outer chamber 100 and the inner chamber 200 is pressed by the cover 300, the locking protrusion 250 is inserted into the insertion space 130 by passing through the stopper 131. Thus, the second sealing member S2 for sealing the plurality of second spaces in the inner chamber 200 is perforated by the protrusion member formed in the outer chamber 100.

The inner chamber 200 is partitioned into the plurality of second spaces 201, 202, 203, 204, and 205 by an inner chamber partition wall. That is, the plurality of second spaces 201, 202, 203, 204, and 205 may be mutually independent spaces.

Upper and lower portions of the plurality of second spaces 201, 202, 203, 204, and 205 are open (i.e., the plurality of second spaces have upper openings and lower openings), upper portions of the plurality of second spaces 201, 202, 203, 204, and 205 are sealed by the first sealing member S1, and lower portions of the plurality of second spaces 201, 202, 203, 204, and 205 are sealed by the second sealing member S2. The first sealing member S1 and the second sealing member S2 may be, for example, films. However, the present disclosure is not limited thereto, and films made of any material through which a fluid does not pass may be used as the first sealing member S1 and the second sealing member S2.

Different reagents are put into the plurality of second spaces 201, 202, 203, 204, and 205, and first, the second sealing member S2 seals the lower portions of the plurality of second spaces 201, 202, 203, 204, and 205, and then the reagents are introduced into the plurality of second spaces 201, 202, 203, 204, and 205, and the first sealing member S1 seals the upper portions of the plurality of second spaces 201, 202, 203, 204, and 205, so that introduction of the reagent into the inner chamber 200 may be completed.

Referring to FIG. 4, the inner chamber 200 includes an upper inner chamber 210 and a lower inner chamber 220.

The upper inner chamber 210 is integrally formed, and when the upper inner chamber 210 is combined with the outer chamber 100, the upper inner chamber 210 is configured to be in close contact with the inner wall of the outer chamber 100.

The lower inner chamber 220 is connected to the upper inner chamber 210 and includes a curved portion so as to be spaced apart from the inner wall of the outer chamber 100 (toward a radially inner side) when the lower inner chamber 220 is combined with the outer chamber 100.

Because the present disclosure uses a dual chamber structure including an inner chamber and an outer chamber, there may be a risk of cross-contamination between reagents in the inner chamber 200 during operation. Cross-contamination can occur via capillary action occurring through a microcavity between the inner chamber and the outer chamber. In the present disclosure, in order to prevent the cross-contamination problem, a structure curved in such a way that the inner chamber 200 is sufficiently spaced from the inner wall of the outer chamber 100 is adopted so that such capillary phenomenon may be prevented.

In addition, in order to prevent the reagent from leaking out through the spaced portion by way of the spaced design of the outer chamber 100 and the inner chamber 200 for preventing capillary action, the upper inner chamber 210 is configured to be in close contact with the inner wall of the outer chamber 100.

On the other hand, by tearing the second sealing member S2 of the inner chamber 200 on the bottom surface of the plurality of first spaces 101, 102, 103, 104, and 105, second protrusion members 111, 112, 113, 114, and 115 that allow the reagent accommodated in the inner chamber 200 to leak out through the plurality of first spaces 101, 102, 103, 104, and 105 protrude.

Each of the second protrusion members 111, 112, 113, 114, and 115 may be disposed to correspond to the plurality of first spaces 101, 102, 103, 104, and 105 in a one-to-one correspondence, for example, a second protrusion member corresponding to reference numeral 111 is configured to tear the second sealing member S2 for sealing the lower portion of the second space corresponding to reference numeral 201, and a second protrusion member corresponding to reference numeral 115 is configured to tear the second sealing member S2 for sealing the lower portion of the second space corresponding to reference numeral 205.

The second protrusion members 111, 112, 113, 114, and 115 include protrusions 111a, 112a, 113a, 114a, and 115a protruding from the bottom surfaces of the plurality of first spaces 101, 102, 103, 104, and 105 by a first height h1, and wing portions 111b, 112b, 113b, 114b, and 115b extending from the protrusions 111a, 112a, 113a, 114a, and 115a and protruding from the bottom surfaces by a second height h2 that is lower than the first height h1. Here, the wing portions 111b, 112b, 113b, 114b, and 115b may have a structure in which they extend in both left and right directions from the protrusions 111a, 112a, 113a, 114a, and 115a.

The protrusions 111a, 112a, 113a, 114a, and 115a serve to perforate the second sealing member S2, and the wing portions 111b, 112b, 113b, 114b, and 115b serve to expand the perforated portion of the second sealing member S2. In the present disclosure, because the height of each of the protrusions 111a, 112a, 113a, 114a, and 115a is higher than that of each of the wing portions 111b, 112b, 113b, 114b, and 115b, a point contact is made between the second sealing member S2 for sealing the lower portion of the inner chamber 200 and the protrusions 111a, 112a, 113a, 114a, and 115a, and through the point contact, there is an effect of minimizing the pressure when the second sealing member S2 is torn. Thus, the second sealing member S2 may be torn with less force.

When the second sealing member S2 is torn by the protrusion members 111, 112, 113, 114, and 115, the reagents stored in the plurality of second spaces 201, 202, 203, 204, and 205 of the inner chamber 200 leak out through the plurality of first spaces 101, 102, 103, 104, and 105 of the outer chamber 100. Then, the leaking reagents are discharged through the first discharge holes 121, 122, 123, 124, and 125 formed through the bottom surfaces of the first spaces 101, 102, 103, 104, and 105. In order to facilitate leaking of the reagents out through the first discharge holes 121, 122, 123, 124, and 125, a portion inclined downwardly toward the first discharge holes 121, 122, 123, 124, and 125 is present in the periphery of the first discharge holes 121, 122, 123, 124, and 125. The inclined portion may have an angle of 3 to 10 degrees. Thus, a procedure in which the reagents leaking out into the first spaces 101, 102, 103, 104, and 105 are discharged through the first discharge holes 121, 122, 123, 124, and 125 may be easily performed.

The cover 300 is coupled to the upper portion of the outer chamber 100 and is configured to cover the upper portions of the outer chamber 100 and the inner chamber 200.

Figure 10:
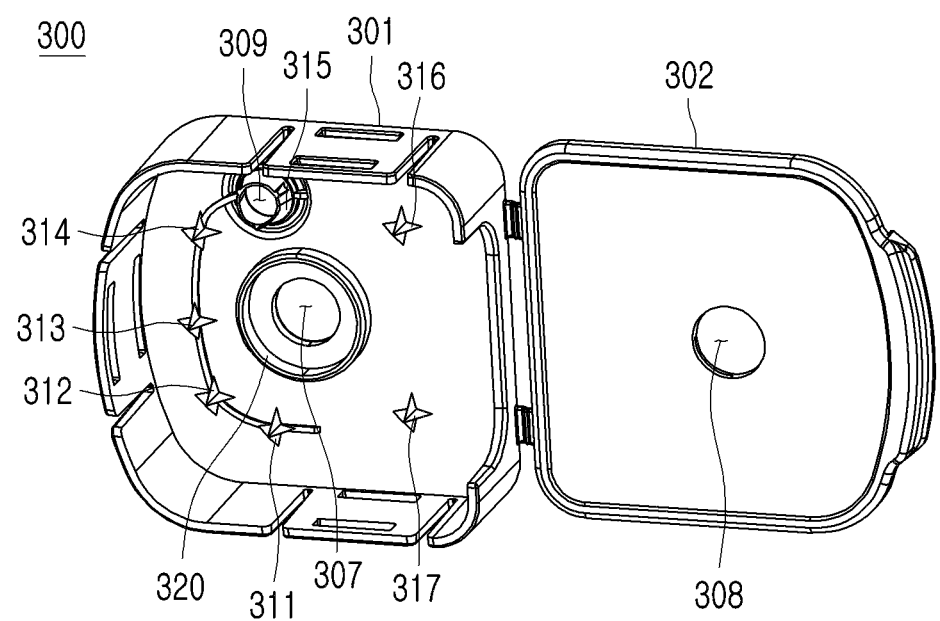
FIG. 10 is a bottom perspective view for describing a cover in more detail.

Referring to FIG. 10, the cover 300 includes a cover body 301 and a cover 302.

The cover body 301 has therein a first insertion hole 307 aligned with the piston insertion portion 108 and a first specimen input hole 309 through which a specimen is inserted (in the attached drawing, the first specimen input hole 309 is aligned with the first space 105 so that the specimen may be introduced into the first space 105 through the first specimen input hole 309), and first protrusion members 311, 312, 313, 314, and 315 for tearing the first sealing member S1 and third protrusion members 316 and 317 for tearing the third sealing member S3 protrude from the bottom surface of the cover body 301.

The first protrusion members 311, 312, 313, 314, and 315 may be disposed to correspond one-to-one with the plurality of first spaces 101, 102, 103, 104, 105, 106, and 107, and the third protrusion members 316 and 317 may be arranged to correspond to the plurality of third spaces 910 and 920 in a one-to-one correspondence. For example, a first protrusion member corresponding to reference numeral 311 is configured to tear the first sealing member S1 for sealing the upper portion of the second space corresponding to reference numeral 201, and a first protrusion member corresponding to reference numeral 315 is configured to tear the first sealing member S1 for sealing the upper portion of the second space corresponding to reference numeral 205.

A separation member 320 is formed on the lower surface of the cover body 301 along the circumference of the first insertion hole 307. The separation member 320 is a portion that allows the first protrusion member and the first sealing member S1 to be spaced apart from each other while the safety clip 500 is combined with the outer chamber 100. That is, as the separation member 320 is supported by the cover support member 541, the cover 300 is spaced apart from the inner chamber 100 by a predetermined distance.

The cover 302 is hinge-rotatably connected to one side of the cover body 301. A second insertion hole 308 aligned with the first insertion hole 307 is formed through the central portion of the cover 302.

In a state in which the cover 300 is coupled to the outer chamber 100, after the safety clip 500 is separated from the outer chamber 100, when the cover 300 is pressed downward, the inner chamber 200 coupled to the outer chamber 100 descends along the inner wall of the outer chamber 100. The second protrusion members 111, 112, 113, 114, 115, 116, and 117 are formed on the bottom surface of the outer chamber 100, and the first protrusion members 311, 312, 313, 314, and 315 and the third protrusion members 316 and 317 are formed on the bottom surface of the cover 300. Thus, the first sealing member S1 and the second sealing member S1 for sealing the upper and lower openings of the inner chamber 200 and the third sealing member S3 for sealing the upper opening of the bead chamber 900 are torn by the protrusion members. Thus, the reagents accommodated in the inner chamber 200 leak out into the plurality of first spaces 101, 102, 103, 104, and 105 of the outer chamber 100, and the second sealing member S2 for sealing the upper opening of the inner chamber 200 is torn so that the reagents may be sufficiently discharged into the first spaces, thereby serving as an air vent.

The base plate 400 is coupled to the lower portion of the outer chamber 100, and includes a plurality of flow paths for guiding a path moving between the first spaces 101, 102, 103, 104, 105, 106, and 107 of the outer chamber 100 and the fluid accommodating portion of the piston 700.

According to an embodiment of the present disclosure, the base plate 400 may include liquid flow paths 401 through 408 through which a liquid can move, and an air flow path 409 through which air can move. A flow cover 410 and a pad 420 may be disposed between the outer chamber 100 and the base plate 400 and may be disposed on the upper surface of the base plate 400 so as to prevent leakage of the liquid when the base plate 400 is combined with the outer chamber 100. When the base plate 400—the flow cover 410—the pad 420 are combined with each other, the upper surfaces of the liquid flow path and the air flow path of the base plate 400 are blocked by the flow cover 410 and the pad 420 so that a space is formed, and thus, a perfect flow path is completed.

The liquid flow paths 401 through 408 are connected to the flow cover 410, the pad 420, and the outer chamber 100 to provide a space in which a specimen and a reagent can be moved and mixed.

The air flow path 409 connects the vacuum control portion of the amplification module 600 and the piston 700 to control the vacuum that may occur when the genome extracted to the amplification module 600 moves, and may prevent contamination of an amplification product that may be generated when the genome is amplified.

In one embodiment, one end of the air flow path 409 communicates with the fluid accommodating portion 701 of the piston 700, and the other end of the air flow path 409 communicates with the amplification module 600, so that the air discharged from the amplification module 600 may pass through the air flow path 409 and may be discharged to the fluid accommodating portion 701.

A plurality of flow paths 401, 402, 403, 404, 405, 406, 407, 408, and 409 are formed on the upper portion of the base plate 400. Each flow path does not cross each other and is formed to extend from the center of the lower body 400 to the outer portion. Here, the liquid flow path is a configuration corresponding to reference numerals 401 through 408, and the air flow path is a configuration corresponding to reference numeral 409.

Figure 14:
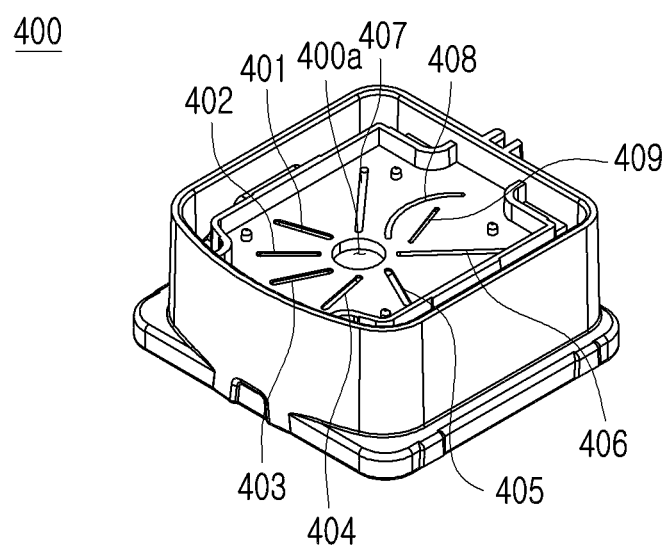
FIG. 14 is a perspective view for describing the base plate in more detail.

Referring to FIG. 14, one end of some of the flow paths may be disposed on the same circumference, and the other end thereof may also be disposed on the same circumference. Among the plurality of flow paths, one end of the air flow path 409 is located on a different circumference from one end of the other liquid flow paths 401 through 408, and the other end thereof is also located on a different circumference from the other ends of the other liquid flow paths 401 through 408 so that the vacuum may be controlled.

A piston driving unit insertion hole 400a is formed through the center of the base plate 400 so that the piston driving unit 800 for rotating the piston 700 may be coupled thereto.

The flow cover 410 is placed in the seating space above the base plate 400. The flow cover 410 may be made of, for example, plastic, and may be ultrasonically welded while being seated on the base plate 400 to be provided integrally with the base plate 400.

The flow cover 410 has a first through hole 410a aligned with the piston driving unit insertion hole 400a, and a plurality of first flow cover holes 411a, 412a, 413a, 414a, 415a, 416a, 417a, and 418a are formed therethrough on a first circumference spaced a first distance from the first through hole 410a, and a plurality of second flow cover holes 411b, 412b, 413b, 414b, and 415b are formed therethrough on a second circumference spaced a second distance from the first through hole 410a, and a plurality of third flow cover holes 416b, 417b, and 418b are formed therethrough on a third circumference spaced a third distance from the first through hole 410a, and fourth flow cover holes 419a and 419b that communicate with one end and the other end of the air flow path 409 are formed therethrough. Here, the first flow cover hole is aligned with the inner end of the flow path formed in the lower body 400, the second flow cover hole and the third flow cover hole are aligned with the other end of the flow path, and the fourth flow cover hole communicates with one end and the other end of the air flow path. The second distance may be longer than the first distance and shorter than the third distance.

Figure 11:
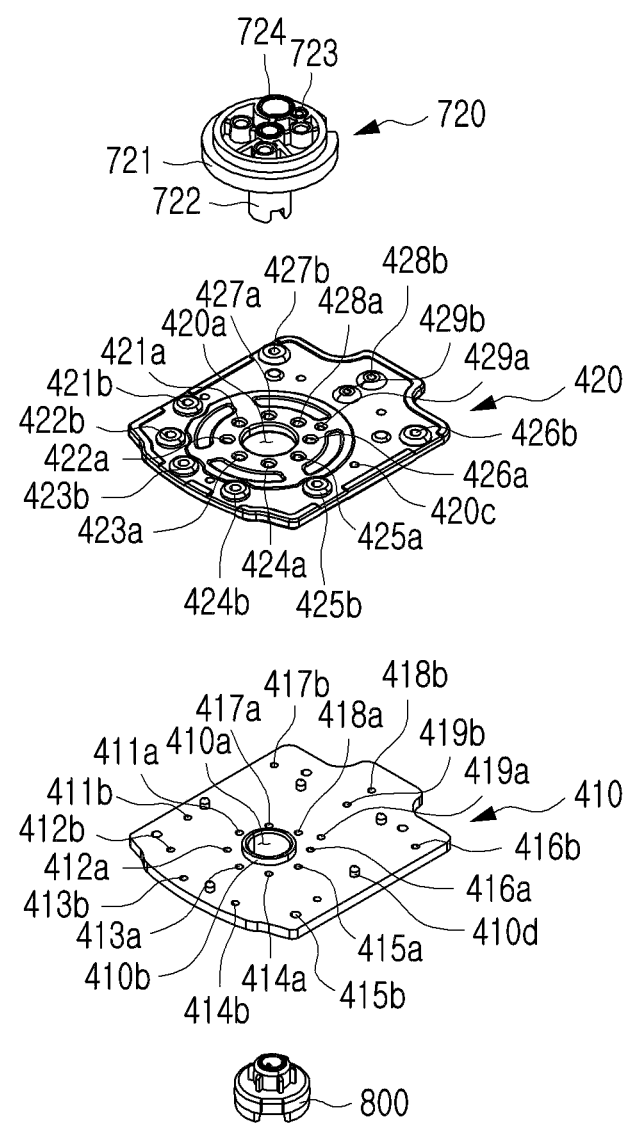
FIG. 11 is an exploded perspective view for describing a flow cover and a pad disposed between a base plate and the outer chamber in more detail.

Referring to FIG. 11, a first coupling protrusion 410b may protrude upward and downward on the outer circumference of the first through hole 410a.

Figure 12:
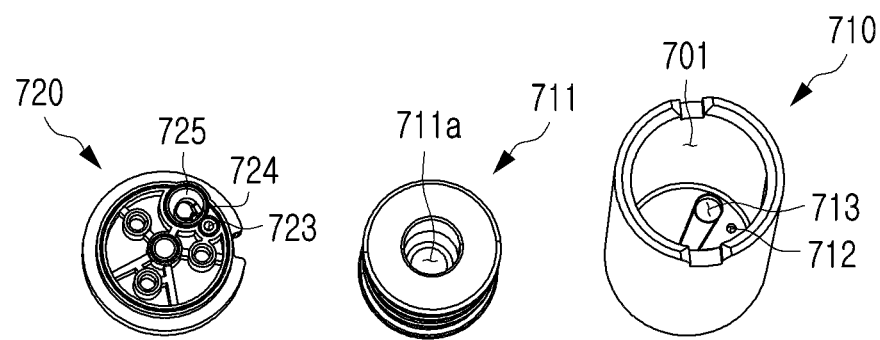
FIG. 12 is an exploded perspective view for describing configurations of a piston in detail.
Figure 13:
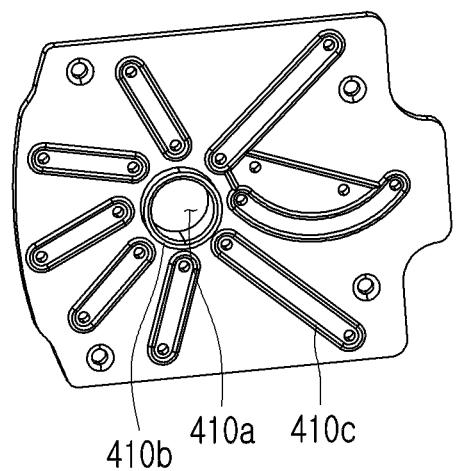
FIG. 13 is a bottom perspective view of the flow cover.

In addition, a melting protrusion 410c coupled along the edge of the plurality of flow paths of the base plate 400 may protrude from the bottom surface of the flow cover 410 (see FIG. 12). When ultrasonic welding is performed after the flow cover 410 is installed on the upper surface of the base plate 400, the melting protrusion 410c is melted and integrated with the base plate 400. Thus, close coupling between the base plate 400 and the flow cover 410 is possible.

A pad 420 is placed on the flow cover 410. The pad 420 may be made of, for example, a silicon material, but any material having a predetermined elastic force may be applied without being particularly limited thereto.

A plurality of second coupling protrusions 410d protrude from the upper surface of the flow cover 410, and the second coupling protrusions 410d are coupled to coupling grooves 420c of the pad 420, so that firm coupling between the flow cover 410 and the pad 420 is performed. Also, the first coupling protrusion 410b of the flow cover 410 is also inserted into the second through hole 420a of the pad 420, so that firm coupling between the two components may be performed.

The pad 420 has a second through hole 420a aligned with the first through hole 410a, and a plurality of first pad holes 421a, 422a, 423a, 424a, 425a, 426a, 427a, and 428a are formed therethrough on a first circumference spaced a first distance from the second through hole 420a, and a plurality of second pad holes 421b, 422b, 423b, 424b, and 425b are formed therethrough on a second circumference spaced a second distance from the second through hole 420a, and a plurality of third pad holes 426b, 427b, and 428b are formed therethrough on a third circumference spaced a third distance from the second through hole 420a, and fourth pad holes 429a and 429b that communicate with one end and the other end of the air flow path 409 are formed therethrough. Here, the first pad hole is aligned with the first flow cover hole, the second pad hole is aligned with the second flow cover hole, the third pad hole is aligned with the third flow cover hole, and the fourth pad hole is aligned with the fourth flow cover hole.

A protrusion that protrudes from a portion in which the plurality of second pad holes 421b, 422b, 423b, 424b, and 425b, the plurality of third pad holes 426b, 427b, and 428b, and the fourth pad hole 429b communicating with the other end of the air flow path are formed and narrows toward the upper side is further formed on the upper surface of the pad 420. Even if the pad 420 is closely disposed between the outer chamber 100 and the base plate 400 through the formation of the protrusion, a problem where the diameter of the pad holes is reduced differently than intended can be solved.

The amplification module 600 is coupled to the outer chamber 100 and is configured to accommodate a pretreated specimen. When the specimen pre-treatment is completed, it means that genomes such as DNA and RNA included in the specimen are lysed in the reagent. When the genome extraction device 1000 according to the present disclosure is coupled to a diagnostic device (not shown), an amplification process (PCR, etc.) of the genome accommodated in the amplification module 600 may be performed.

Referring to FIGS. 1 and 2, the amplification module 600 is coupled to the outer chamber 100 in a vertical direction. In other words, an upper portion 631 of an accommodating portion 630 of the amplification module 600 is coupled to the outer chamber 100 so as to be farther from the ground than a lower portion 632.

Referring to FIGS. 17 through 25, the amplification module 600 includes a body 610, injection ports 621 and 622, the accommodating portion 630, a gas moving passage 640, and an extract moving passage 650.

The body 610 is a portion forming the outer shape of the amplification module 600, and the injection ports 621 and 622 coupled to the discharge holes 128 and 129 of the outer chamber 100 are formed on one side of the body 610.

The injection ports 621 and 622 are coupled to the discharge holes 128 and 129 to serve as an inlet for the extract discharged from the discharge holes 128 and 129 to be introduced into the accommodating portion 630.

The amplification module 600 according to an embodiment of the present disclosure may have two injection ports 621 and 622, but the present disclosure is not particularly limited thereto, and an embodiment having a number of injection ports greater than two may also be included in the scope of the present disclosure.

Hereinafter, it will be described in detail on the assumption that the amplification module 600 according to an embodiment of the present disclosure has two injection ports 621 and 622.

One injection port 621 of the two injection ports 621 and 622 communicates with the air flow path 409, and the other injection port 622 communicates with the liquid flow path 408. That is, the extract containing the pre-treated specimen is introduced through the other injection port 622, and in this process, the air in the accommodating portion 630 is discharged to the air flow path 409 through any one injection port 621.

The accommodating portion 630 that accommodates the extract introduced through the injection port 621 is formed on the other side of the body 610.

In one example, the accommodating portion 630 may be manufactured in a form that penetrates both one surface and the opposite surface of the body 610, but in another embodiment, the accommodating portion 630 may be manufactured in a form that penetrates only one surface and does not penetrate the opposite surface. Both embodiments are identical in that the open portion is sealed by a sealing member. Accordingly, the extract and air are introduced or discharged only through the gas moving passage 640 and the extract moving passage 650.

Figure 17:
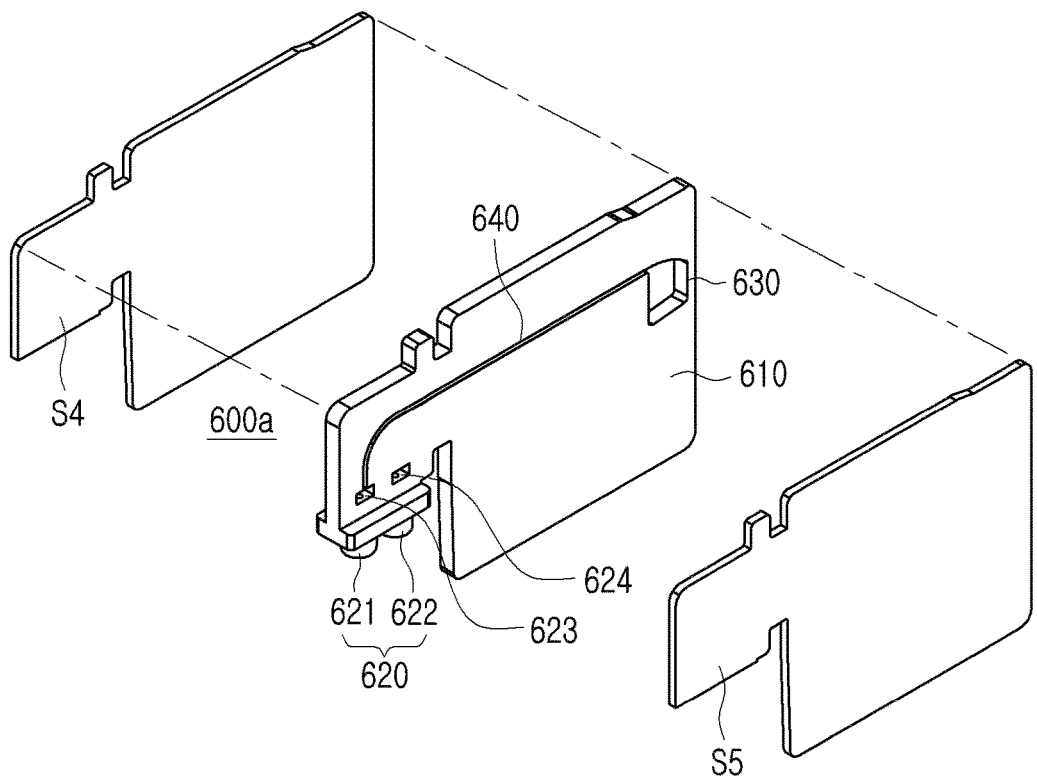
FIGS. 17 through 19 are views for describing an amplification module according to a first embodiment of the present disclosure.
Figure 18:
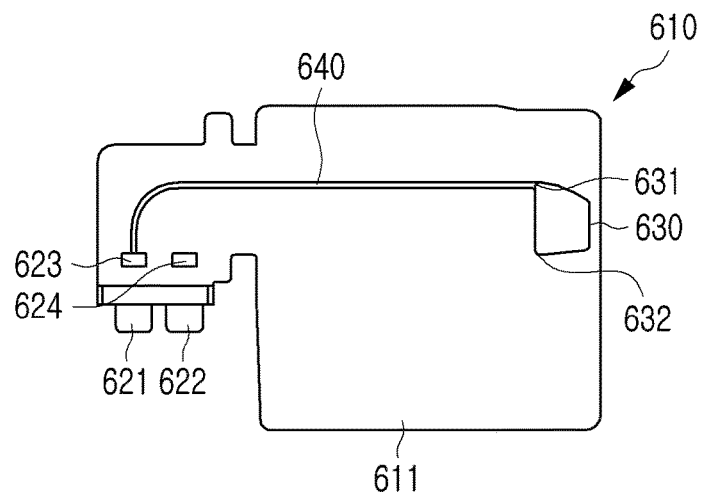
Figure 19:
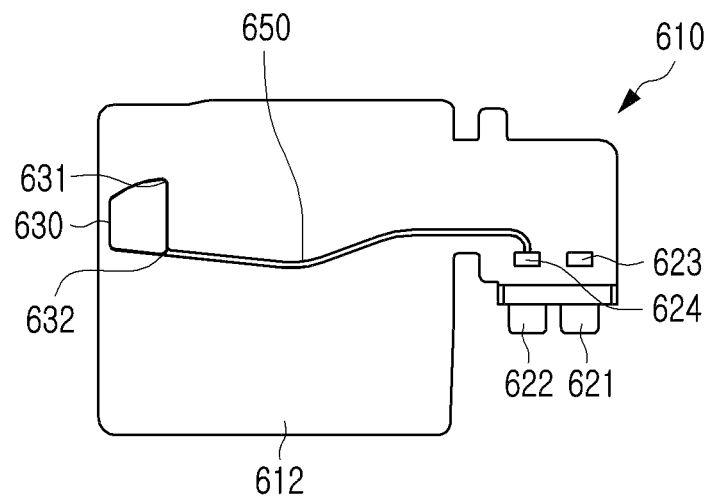
Figure 20:
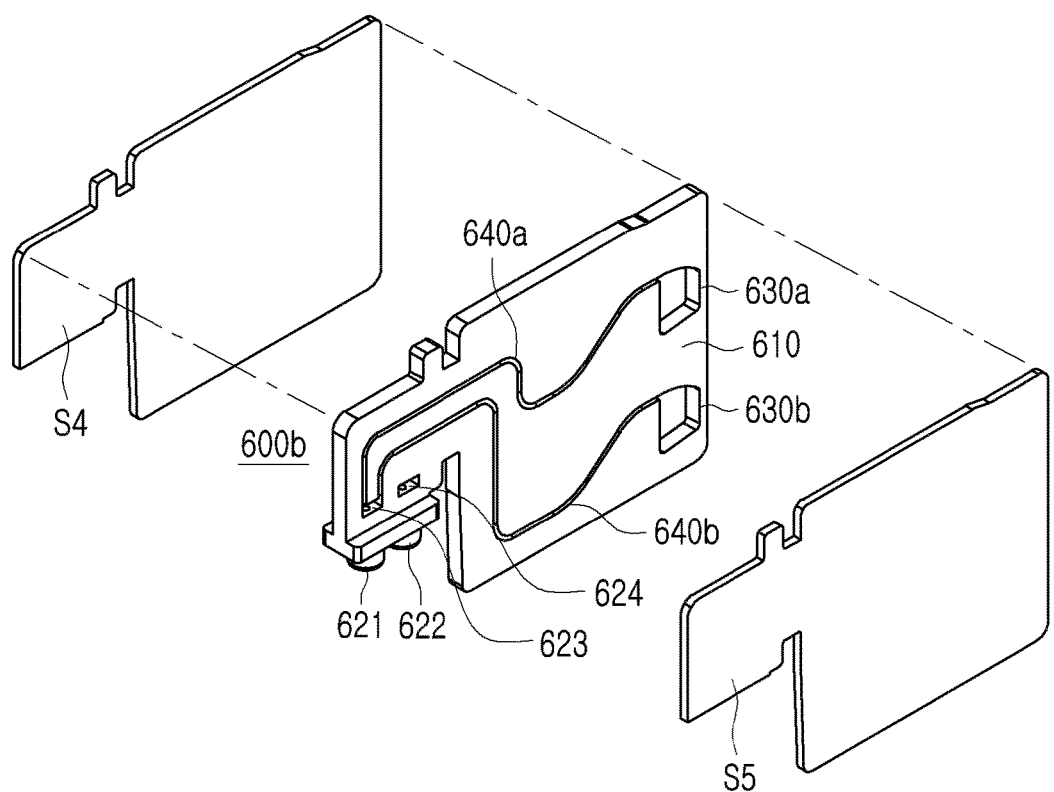
FIGS. 20 through 22 are views for describing an amplification module according to a second embodiment of the present disclosure.
Figure 23:
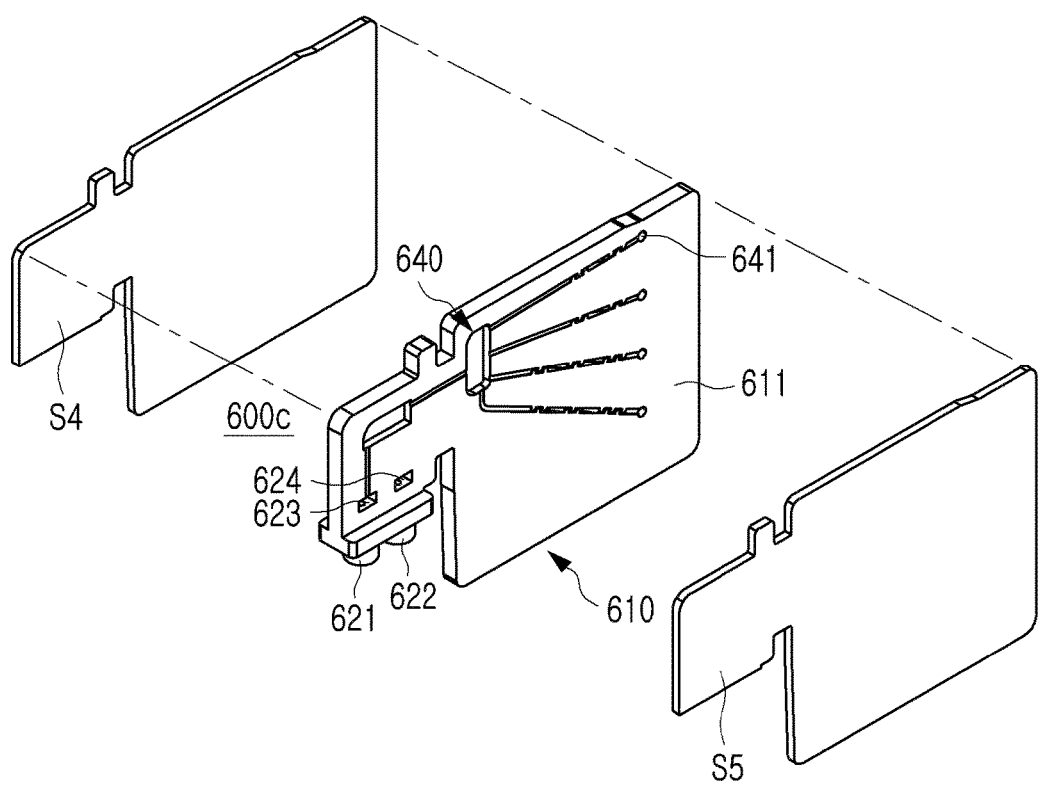
FIGS. 23 through 25 are views for describing an amplification module according to a third embodiment of the present disclosure.

One or more accommodation portions 630 according to an embodiment of the present disclosure may be provided in one amplification module 600. FIG. 17 shows an amplification module having one accommodating portion, FIG. 20 shows an amplification module having two accommodating portions, and FIG. 23 shows an amplifying module having four accommodating portions.

The accommodating portion 630 may have a substantially trapezoidal shape, and more specifically, it may preferably have a trapezoidal shape with rounded edges.

Here, the trapezoidal shape means a shape in which the width becomes narrower as the distance from the gas flow path 640 and the extract moving passage 650 increases. By having the accommodating portion 630 having the above shape, a problem where bubbles are generated even when the extract is injected through the extract moving passage 650 is solved. If the bubbles remain in the accommodating portion 630, there is a problem of detection failure that may occur in a fluorescence detection process after the amplification process. Thus, the problem may be solved through the shape of the accommodating portion 630.

Primers and probes necessary for genome amplification are provided in the accommodating portion 630. The amplification module 600 according to an embodiment of the present disclosure is provided with one or more accommodating portions 630, and different types of primers and probes may be provided in each accommodating portion 630. Thus, a plurality of detection processes can be simultaneously performed on a genome extracted from a single specimen. For example, one accommodating portion 630a is provided with a primer and a probe for coronavirus amplification, and the other accommodating portion 630b is provided with a primer and a probe for influenza virus amplification, so that various detection processes may be performed in one amplification module 600 at the same time.

The gas moving passage 640 is formed on one surface 611 of the body 610 and is configured to connect an injection port 621 and an upper portion 631 of the accommodating portion 630. On the contrary, the extract moving passage 650 is formed on an opposite surface 612 to the one surface 611 and is configured to connect an injection port 622 and a lower portion 632 of the accommodating portion 630.

The gas moving passage 640 serves as a passage through which the gas in the accommodating portion 630 moves. The flow path of the amplification module 600 communicates with the genome extraction device 100 and at the same time has a closed flow path. Because the accommodating portion 630 is in a state of being filled with air before the extract is injected, if the extract is injected, air of a suitable capacity is required to be discharged to the outside. In the present disclosure, as the air inside the accommodating portion 630 through the gas moving passage 640 is discharged to the air flow path 409 through the injection port 621, an air bubble problem caused by the air remaining with the pressure reduction in the accommodating portion 630 has also been solved. The gas moving passage 640 is also provided in a curved shape without an angled portion like the accommodating portion 630 to minimize the generation of air bubbles.

Because the gas is lighter than the liquid, such as the extract, the gas moving passage 640 is connected to the end of the upper portion 631 of the accommodating portion 630.

When a plurality of accommodating portions 630 are provided, preferably, the lengths of the gas moving passages 640 connected to each accommodating portion 630 are different from each other.

In the case of the embodiment in which a plurality of accommodating portions 630 are provided, the extract is injected from the accommodating portion located at the lower portion, and the extract is injected at a more delayed time as the accommodating portion located at the upper side is increased. Thus, depending on the formation position of the accommodating portion 630, the time at which air is discharged from the corresponding accommodating portion 630 will also be different. In other words, the air is discharged through the gas moving passage 640 more quickly as the accommodating portion is located at the lower portion.

In addition, not only the air in the accommodating portion 630 but also the extract injected into the accommodating portion 630 may be discharged through the gas moving passage 640. Because the plurality of gas moving passages 640 are connected to one another, the extract discharged through any one gas moving passage 640 is introduced into another accommodating portion along the other gas moving passage 640 so that a problem may occur in which the extract or amplification product is mixed. In order to solve the above problem, in the present disclosure, the gas moving passage 640 connected to the accommodating portion 630 located at the lower portion is formed to have a larger length, thereby solving the problem of mixing the extract or the amplification product.

Figure 21:
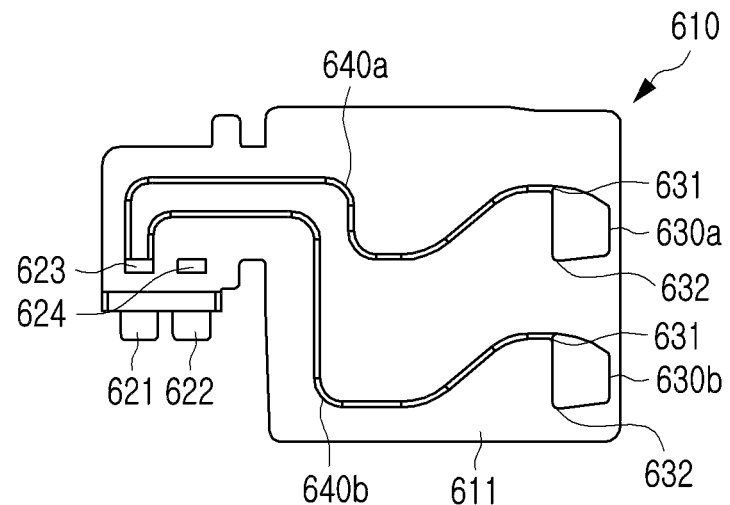
Figure 22:
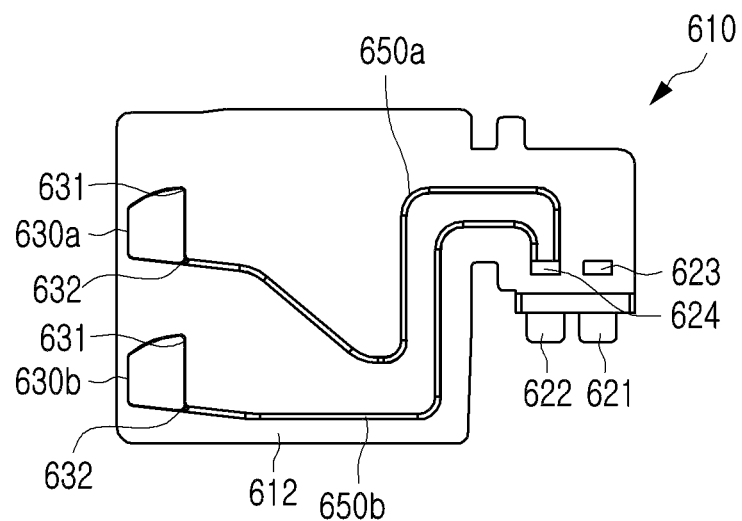
Figure 24:
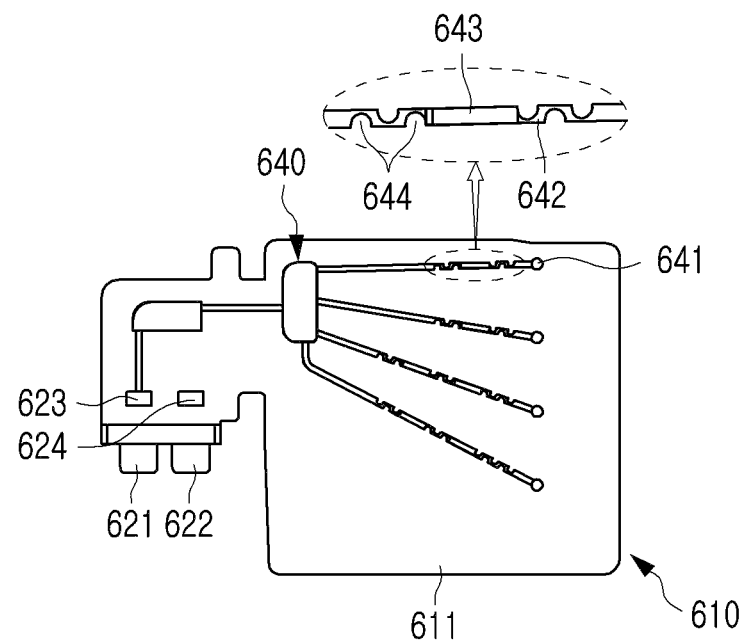

A method of varying the length of the gas moving passages 640 from one another may be configured as shown in FIG. 21 or FIG. 24.

Referring to FIG. 24, the gas moving passage 640 includes a communication hole 641 that is formed in one surface 611 of the body 610, communicates with a gas discharge passage 633 connected to the upper portion 631 of the accommodating portion 630, and perforates the body 610, a moving passage 642, a storage passage 643, and a passage pattern forming portion 644.

The passage pattern forming portion 644 is configured in such a way that a predetermined passage pattern is formed in the moving passage 642. When FIG. 24 is taken as an example, the passage pattern forming portion 644 may have a semicircular shape, and the semicircular passage pattern forming portion 644 is combined with the linear moving passage 642 so that a passage pattern as shown in FIG. 24 may be manufactured. The passage pattern forming portion 644 may form the passage pattern shown in FIG. 24 while being alternately combined with the moving passage 642 on the left and right sides of the linear moving passage 642. Here, the combination means that the empty space of the moving passage 642 is filled in the shape of the passage pattern forming portion 644, so that the fluid does not pass through the filled space.

That is, the portion of the gas moving passage 640 combined with the passage pattern forming portion 644 corresponds to the moving passage 642, and the portion of the gas moving passage 640 that is not combined corresponds to the storage passage 643.

The length of the gas moving passage 640 increases in proportion to the number of passage pattern forming portions 644 combined and as the number of storage passages 643 increases, and the accommodating portion located at the lower portion has a large number of the passage pattern forming portions 644 and the storage passages 643. Thus, mixing of the extract or the amplification product accommodated in the accommodating portion 630 may be prevented.

The extract moving passage 650 is formed on the opposite surface 612 to the one surface 611 of the body 610 and is configured to connect the injection port 622 and the lower portion 632 of the accommodating portion 630. The extract moving passage 650 serves as a passage through which the extract pretreated in the dielectric extraction apparatus 1000 moves.

In the extract moving passage 650, in order to prevent mixing of the extract or amplification product accommodated in the accommodating portion 630 or in order to allow the same amount of the extract to be introduced into each accommodating portion 630, when a plurality of accommodating portions 630 are provided, the length of each of the extract moving passages 650 may be the same, or when the lengths of the extract moving passages 650 are different from each other, the thicknesses of the extract moving passages 650 may be different from each other.

In addition, in order to prevent the occurrence of air bubbles during the movement of the extract through the extract moving passage 650, the extract moving passage 650 is provided in a curved form without an angled portion to minimize the occurrence of air bubbles.

Figure 25:
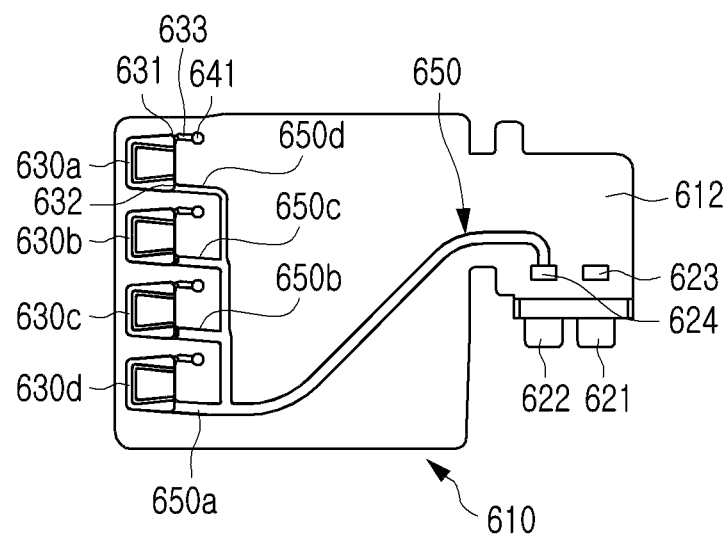

Referring to FIG. 25, the extract moving passage 650 extends from the injection port 622 and branches at one point. From the point of branching, the lower accommodating portion becomes thicker and the upper accommodating portion becomes thinner. The thinner the passage, the faster the extract passes, so that the same amount of extract can be injected regardless of the upper and lower accommodating portions.

The piston 700 is inserted into the piston insertion portion 108 of the outer chamber 100 and is configured to inhale the reagent accommodated in the outer chamber 100 according to the lifting and lowering movement or to discharge the reagent inhaled into the outer chamber 100 or the amplification module 600.

Figure 3:
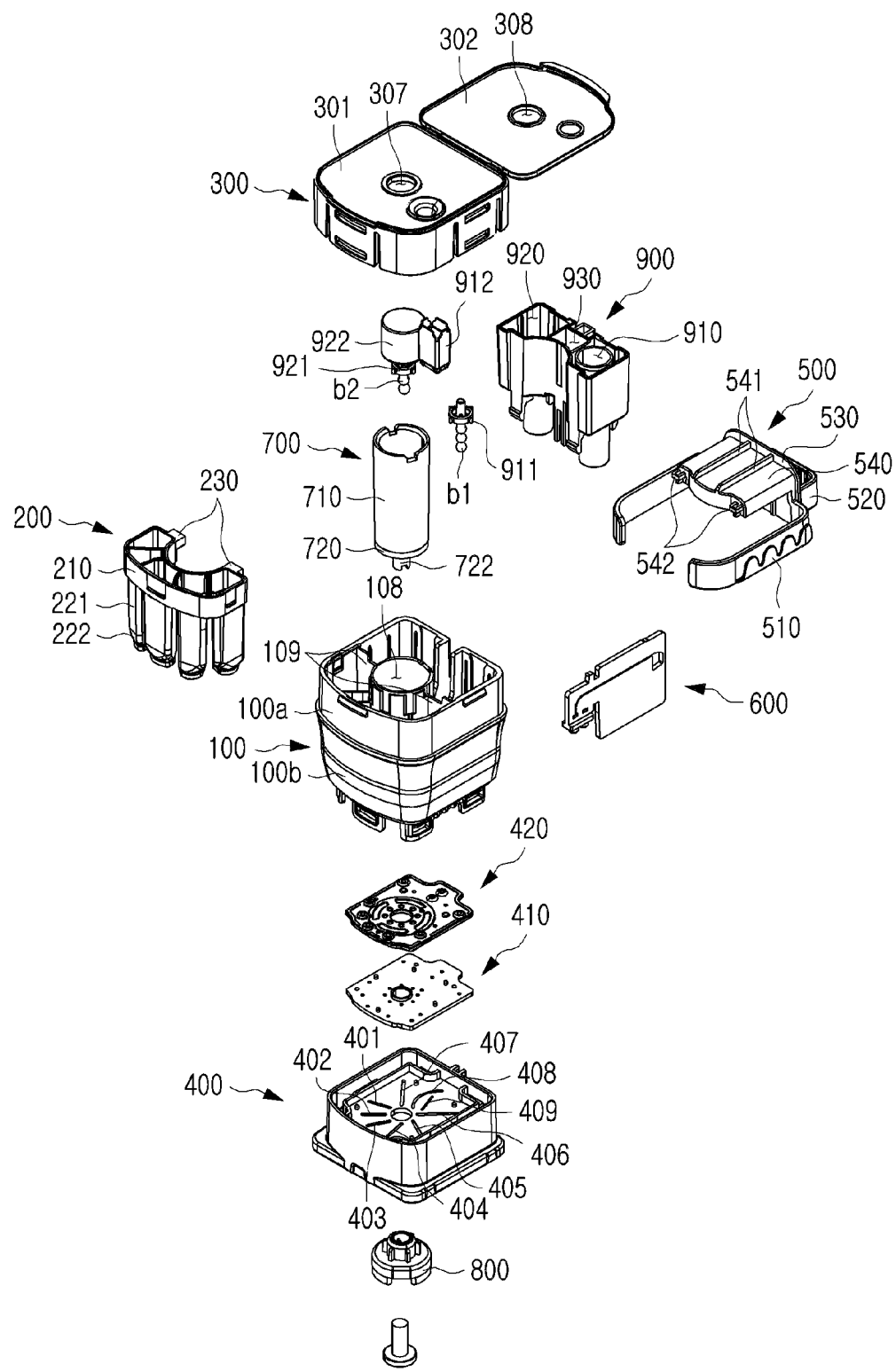
FIG. 3 is an exploded perspective view of FIG. 1.

Referring to FIGS. 3 and 12, the piston 700 includes an upper piston 710 and a lower piston 720.

The upper piston 710 has an open upper portion, and a fluid accommodating portion 701 in which inhaled fluids are accommodated is formed in the upper piston 710. A close contact portion 711 is installed inside the upper piston 710. The outer surface of the close contact portion 711 is in close contact with the inner surface of the upper piston 710, so that the fluids cannot enter and exit through a space between the outer surface of the close contact portion 711 and the inner surface of the upper piston 710. A driving unit installation portion 711a to which a driving unit (not shown) of the diagnostic device is coupled is recessed in the center of the close contact portion 711. The driving unit (not shown) of the diagnostic device is coupled to the driving unit installation portion 711a, and by lifting and lowering the close contact portion 711 inside the upper piston 710, the fluids are inhaled into the fluid accommodating portion 701, or the fluids accommodated in the fluid accommodating portion 701 are discharged to the outside.

A coupling structure engaged with the lower piston 720 may be formed on the bottom surface of the upper piston 710, and a first hole 712 connected to a liquid port of the lower piston 720 and a second hole 713 connected to a filter port of the lower piston 720 are formed through the upper piston 710. The second hole 713 may be formed to have a smaller diameter than a filter seating space of the filter port to prevent separation of the support structure and the filter.

The lower piston 720 is fixed in engagement with the coupling structure formed on the bottom surface of the upper piston 710.

The lower piston 720 has a disk-shaped body 721, a shaft 722 formed to protrude from the center of the body 721 to the outside, and a liquid port 723 and a filter port 724, which are disposed at the same distance from the center of the body 721.

The liquid port 723 is used to inhale, mix, and discharge specimens and reagents into the piston 700, and the filter port 724 may be used to clean a genome collection filter or to separate the genome from the genome collection filter.

In addition, a groove recessed in the central direction may be formed on the outer periphery of the body 721 of the lower piston 720. This groove serves to remove vacuum that may occur during liquid movement inside the genome extraction device.

The liquid port 723 and the filter port 724 are disposed at a certain angle apart from each other on the same circumference. For example, two ports of the filter port 724 and the liquid port 723 may be spaced apart from each other by 18 degrees to 36 degrees, and more specifically, the two ports may be spaced apart from each other by 22.5 degrees. When a step motor that is divided into 16 circuits to perform one rotation is used, the positions of the liquid port 723 and the filter port 724 may be changed by one driving.

The filter port 724 of the lower piston 720 may include a filter seating space 725, and a filter and a support structure may be disposed in the filter seating space 725. A glass fiber filter having various particle sizes may be used as a filter for collecting genome, and the support structure serves to fix the filter for collecting genome.

The support structure may be formed of a porous plastic material having a constant particle size to prevent separation of the filter and maintain a constant pressure when the fluid is discharged.

The driving unit 800 is connected to a driving unit (not shown) of the diagnostic device and serves as a medium for rotating the piston 700 at a predetermined angle.

The driving unit 800 may include a coupling groove formed to engage with a shaft 722 in a central portion of one surface and a driving groove formed to engage with the driving unit (not shown) of the diagnostic device on the other surface.

The driving unit 800 is coupled to the piston 700 to move the liquid port 723 and the filter portion 724 to suitable positions of the first discharge holes of the outer chamber 100 so as to perform various chemical reactions required in the genome extraction operation inside one device.

The liquid port 723 and the filter port 724 are spaced apart from each other by a predetermined angle, and the driving unit 800 rotates the ports to suitable positions for each operation during genome extraction.

The bead chamber 900 includes a first bead chamber 910, a second bead chamber 920, and a dehumidification chamber 930, which are partitioned by a first bead chamber partition wall 901 and a second bead chamber 902. The first bead chamber 910 is inserted into the first space 106 of the outer chamber 100, and the second bead chamber 920 is inserted into the first space 107 of the outer chamber 100.

Like in the inner chamber 200, the upper opening of the bead chamber 900 is also sealed by the third sealing member S3, and the third sealing member S3 is perforated by the third protrusion members 316 and 317 formed on the bottom surface of the cover 300 when the cover 300 is coupled to the outer chamber 100. The upper opening of the bead chamber 900 is opened by the third protrusion members 316 and 317, so that even if the fluid is then introduced into the first bead chamber 910 and the second bead chamber 920, a corresponding amount of air may be discharged through the perforated portion.

The lower opening of the bead chamber 900 is not separately sealed by a sealing member and is provided in an open form. Dry beads (more specifically freeze-dried beads) are stored in the bead chamber 900, and the dry beads have a property of being vulnerable to moisture. In the genome extraction device according to the present disclosure, the lower opening of the bead chamber 900, the first space of the outer chamber 100, the flow cover 410, the pad 420, the flow path of the base plate 400, and the flow path of the amplification module 600 communicate with each other, and a closed flow path that is not exposed to the outside air is formed so that the inflow of moisture into the bead chamber 900 is minimized.

A plurality of dry beads b1 necessary for genome extraction may be stored in the first bead chamber 910, and a plurality of dry beads b2 necessary for genome amplification may be stored in the second bead chamber 920.

A first bead holder 911 configured to maintain the dry beads b1 not to be discharged to the outside but to be inside is installed in the upper opening of the first bead chamber 910, and a first dehumidifying unit 912 for dehumidifying an internal space of the first bead chamber 910 is installed. Here, the dry beads necessary for genome amplification may be provided in, for example, a capsule form, but the present disclosure is not particularly limited thereto.

A second bead holder 921 configured to maintain the dry bead b2 not to be discharged to the outside but to be inside is installed in the upper opening of the second bead chamber 920, and a second dehumidifying unit 922 for dehumidifying the inside of the chamber 920 is installed on the second bead holder 921. The third sealing member S3 seals the second bead chamber 920 so that the dehumidification chamber 930 and the first bead chamber 910 do not communicate with each other but the first bead chamber 910 and the dehumidification chamber 930 communicate with each other. This will be described in detail with reference to FIGS. 26 and 27.

Figure 26:
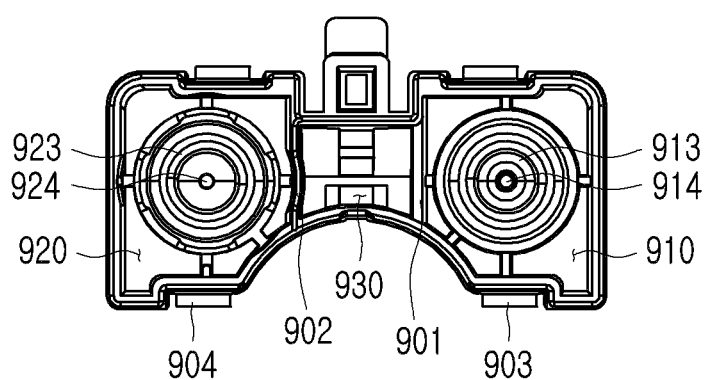
FIG. 26 is a plan view of a bead chamber.
Figure 27:
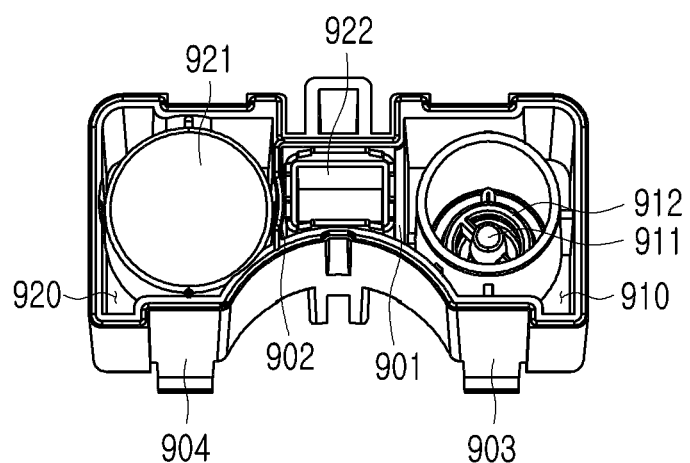
FIGS. 27 and 28 are perspective views for describing the configuration of the bead chamber in more detail.

The above-described effect is achieved through the configuration of the height difference between the first bead chamber partition wall 901 and the second bead chamber partition wall 902. Referring to FIGS. 26 and 27, the second bead chamber partition wall 902 partitioning the second bead chamber 920 and the dehumidification chamber 930 has a greater height than the first bead chamber wall 901 partitioning the first bead chamber 910 and the dehumidification chamber 930.

In other words, the upper portion of the second bead chamber partition wall 902 extends to the same height as the upper portion of an outer partition wall constituting the second bead chamber 920, and the upper portion of the first bead chamber partition wall 901 extends to a height less than that of an outer partition wall constituting the first bead chamber 910.

Thus, even if the upper opening of the bead chamber 900 is sealed by the third sealing member S3, the first bead chamber 910 and the dehumidification chamber 930 may communicate with each other through a space between the first bead chamber partition wall 901 and the third sealing member S3. Thus, the first bead chamber 910 is dehumidified by the second dehumidifying unit 912 installed inside the dehumidification chamber 930.

The lower opening 912 of the first bead chamber 910 (i.e., an outlet of the first bead chamber) and the lower opening 922 of the second bead chamber 920 (i.e., an outlet of the second bead chamber) are formed at the ends of the discharge passages 911 and 921 that become narrower toward the base plate 400 from the bead chamber 900.

Dry beads may be accommodated in the discharge passages 911 and 921, and bead holders are installed on the discharge passages 911 and 921 to prevent the beads accommodated in the discharge passages 911 and 921 from leaking out to the outside.

The discharge passages 911 and 921 may have a so-called tapered shape that becomes narrower toward the base plate 400. In addition, the diameters of the lower openings 912 and 922 located at the ends of the discharge passages 911 and 921 are smaller than the diameter of the dried beads, so that the beads are not discharged to the outside through the lower openings 912 and 922. The fluid flows into the discharge passages 911 and 921 through the lower openings 912 and 922, the introduced fluid melts the dry beads, and the dry beads may be discharged to the outside (the fluid accommodating portion of the piston or amplification module) through the lower openings 912 and 922 only through the form of a fluid.

Here, the discharge passage 911 of the first bead chamber 910 in which dry beads necessary for genome amplification are stored has a wider diameter than the discharge passage 921 of the second bead chamber 920 and may become narrower toward the base plate 400.

Before the extract pre-treated toward the amplification module 600 is input, a configuration in which the last fluid is input, corresponds to the first bead chamber 910. Because the fluid injected into the first bead chamber 910 does not remain as much as possible in the first bead chamber 910 and is required to be put into the accommodating portion 630 of the amplification module 600 to obtain an accurate detection result, in the present disclosure, the discharge passage 911 of the first bead chamber 910 has a wider diameter than the discharge passage 921 of the second bead chamber 920 and becomes narrower so that the residual amount of the fluid in the first bead chamber 910 is minimized.

Figure 28:
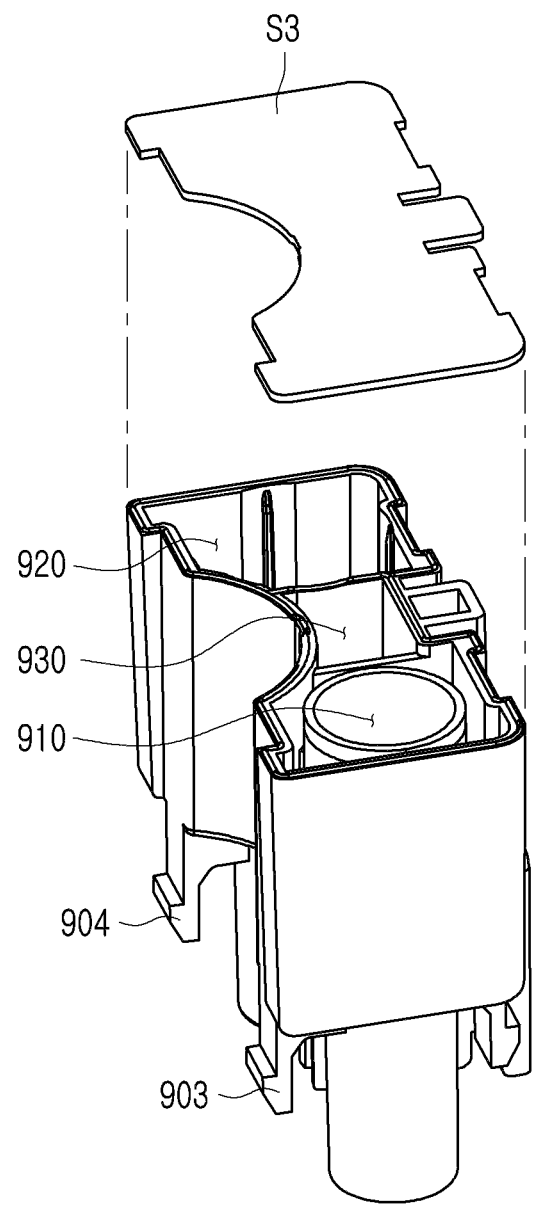
Figure 29:
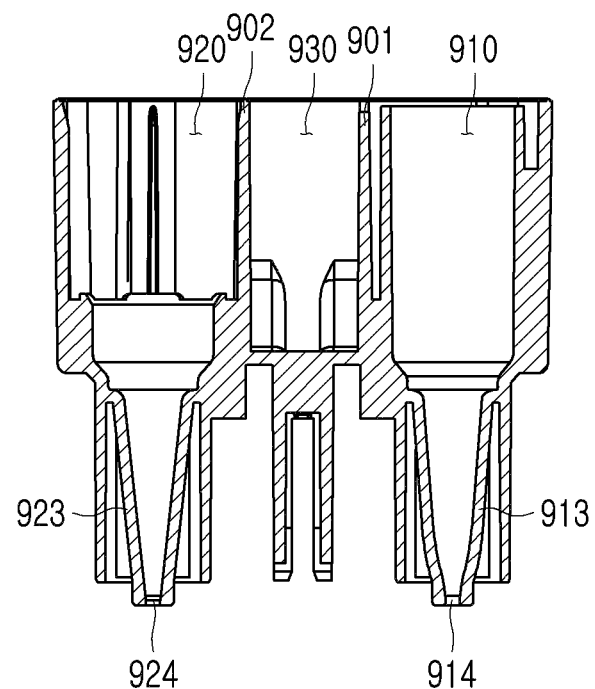
FIG. 29 is a cross-sectional view of the bead chamber of FIG. 28.
Figure 30:
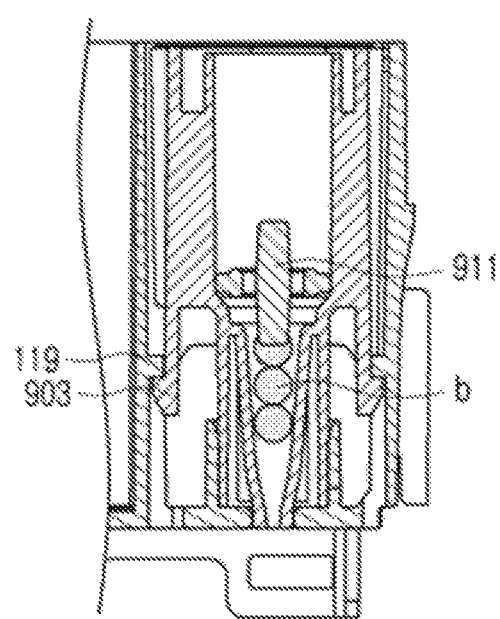
FIG. 30 is a longitudinal cross-sectional view of the bead chamber of FIG. 28 and is a view for describing a structure in which the bead chamber is combined with the outer chamber.

In addition, the bead chamber 900 according to the present disclosure has first locking protrusions 903 and 904 extending from the bottom surfaces of the outer partition walls of the first bead chamber 910 and the second bead chamber 920. As shown in FIGS. 28 and 30, the first locking protrusions 903 and 904 may be formed in a structure that extends toward the base plate 400 and then protrudes outward.

In the outer chamber 100 coupled to the bead chamber 900, a second locking protrusion 109 is formed on one side of the outer chamber partition wall partitioning the plurality of first spaces, and force is applied to the bead chamber 900 in a direction of the base plate 400 so that the first locking protrusions 903 and 904 pass through the second locking protrusions 109 and are coupled to each other, and thus, firm coupling between the two components can be made. When the first locking protrusions 903 and 904 are coupled to the second locking protrusions 109, the relative position of the bead chamber 900 with respect to the outer chamber 100 is fixed.

Hereinafter, an extraction method according to an embodiment of the present disclosure will be described in detail.

First, (a) an inner chamber is coupled to an outer chamber through the upper openings of the plurality of first spaces of the outer chamber. Here, preferably, the fixing portion of the inner chamber is coupled to the outer chamber while being coupled to the inner chamber coupling portion of a safety clip.

Next, (b) a cover is coupled to the outer chamber, and (c) the safety clip is removed from the outer chamber.

Next, (d) the cover is pressed, and a first sealing member for sealing the upper opening of the inner chamber is torn by a first protrusion member formed on the bottom surface of the cover, and a second sealing member for sealing the lower opening of the inner chamber is torn by a second protrusion member formed on the bottom surfaces of a plurality of first spaces of the outer chamber, so that reagents accommodated in the inner chamber leak out through the plurality of first spaces, and (e) by driving of a driving unit, the reagents leaking out through the plurality of first spaces are inhaled into a fluid accommodating portion inside an upper piston and are mixed with each other, and then the mixed reagents are discharged to an amplification module.

Operation (e) may include a plurality of operations. Hereinafter, operation (e) will be described in more detail below.

First, (e1) a specimen to be analyzed is introduced into one of the plurality of first spaces of the outer chamber through a specimen input hole of the cover.

Next, (e2) a piston installed in a piston accommodating portion of the outer chamber rotates, so that a liquid port of the piston and first discharge holes formed through the bottom surface of any one of the first spaces into which the specimen to be analyzed is put communicate with each other.

Next, (e3) a close contact portion installed in the inner space of the piston is lifted so that the specimen to be analyzed accommodated in any one of the first spaces is inhaled into the fluid accommodating portion inside the outer chamber.

Next, (e4) the piston rotates so that the liquid port of the piston and the first discharge holes formed through the bottom surface of the other first space communicate with each other.

Next, (e5) the close contact portion is lifted so that a first reagent accommodated in the other first space is inhaled into the fluid accommodating portion inside the outer chamber, and thus, the specimen to be analyzed and the first reagent are mixed in the fluid accommodating portion.

Next, (e6) the piston rotates, so that the liquid port of the piston and first discharge holes formed through the bottom surface of another first space communicate with each other.

Next, (e7) the close contact portion is lifted so that a second reagent accommodated in the other first space is inhaled into the fluid accommodating portion inside the outer chamber, and thus, the specimen to be analyzed, the first reagent, and the second reagent are mixed with each other.

Next, (e8) the piston rotates so that the filter port of the piston and first discharge hole formed through the bottom surface of another first space communicate with each other.

Next, (e9) the close contact portion is lowered so that a mixed solution accommodated in the fluid accommodating portion passes through a genome collection filter installed in the filter port and is discharged into another first space.

Next, (e10) the piston rotates, so that the liquid port of the piston and first discharge holes formed through the bottom surface of the first space in which the first reagent, the second reagent, and other reagents are accommodated communicate with each other.

Next, (e11) the close contact portion is lifted so that other reagents are inhaled into the fluid accommodating portion and are mixed with each other.

Next, (e12) the piston rotates, so that the filter port of the piston and first discharge holes formed through the bottom surface of the first space in which other reagents are accommodated communicate with each other.

Next, (e13) the close contact portion is lowered so that the mixed solution accommodated in the fluid accommodating portion passes through the genome collection filter and is discharged into the first space in which other reagents are accommodated.

Next, (e14) the piston rotates so that the liquid port of the piston and first discharge holes formed through the bottom surface of the first space in which an eluent is accommodated communicate with each other.

Next, (e15) the close contact portion is lifted so that the eluent is inhaled into the fluid accommodating portion.

Next, (e16) the piston rotates so that the filter port of the piston and a second discharge hole formed in the bottom surface of the first space in which beads required for genome amplification are accommodated communicate with each other.

Next, (e17) the close contact portion is lowered so that the eluent contained in the fluid accommodating portion passes through the genome collection filter and is discharged to the first space in which the beads required for genome amplification are accommodated, and a genome collected by the genome collection filter is separated from the genome collection filter and is discharged together into the first space.

Next, (e18) the piston rotates so that the liquid port of the piston and a second discharge hole formed in the bottom surface of the first space in which the genome is accommodated communicate with each other.

Next, (e19) the close contact portion is lifted so that the extract containing the genome is inhaled into the fluid accommodating portion.

Next, (e20) the piston rotates so that that the liquid port of the piston and the amplifying module communicate with each other.

Next, (e21) the close contact portion is lowered so that the extract containing the genome contained in the fluid accommodating portion is discharged to the amplification module.

Next, (e22) the extract is introduced into the accommodating portion of the amplification module through the extract moving passage of the amplification module.

Next, (e23) the air remaining in the accommodating portion is discharged to the outside of the amplification module through the gas moving passage of the amplification module.

Next, (e24) an amplification device applies heat of a predetermined temperature or higher to the accommodating portion to amplify the genome.

Next, (e25) it is determined whether the specimen to be analyzed is infected with a disease, based on fluorescent intensity of an amplification product of the genome.

In the genome extraction device according to the present disclosure, an inner chamber in which reagents required for genome extraction are accommodated is provided separately from the outer chamber, and the upper and lower portions of the inner chamber are sealed so that a problem where the reagent accommodated in a single chamber in a genome extraction device according to the related art leaks out can be solved.

In addition, as the inner chamber moves up and down due to vibration generated during the production and distribution process of a product, the sealing member for sealing the upper opening and the lower opening of the inner chamber can be prevented from being perforated by protrusion members formed in a cover and the outer chamber.

In addition, the problem of cross-contamination between reagents due to capillary action occurring through a space between dual chambers is solved.

In addition, in a structure for preventing the capillary action, the reagents can be prevented from leaking out.

In addition, by using the configuration of the protrusion member formed on the bottom surface of the outer chamber, the sealing member can be torn even with a small force, and the perforated portion is expanded, so that the reagent contained in the inner chamber leaks out smoothly to the outside.

In addition, an inclined portion is formed around a discharge hole through which the reagents are discharged, so that the reagents are smoothly discharged through the discharge hole.

In addition, by disposing a dual-structured flow cover-pad between the outer chamber and the base plate, the convenience of manufacturing is improved and the problem of unintentionally narrowing a flow path is solved compared to a genome extraction device according to the related art in which only one pad is disposed can be solved.

In addition, firm coupling between the base plate, the flow cover, the pad, and the outer chamber is achieved, so that sealed flow paths are formed without the phenomenon of leaking out from the middle during the movement of the reagents.

In addition, a bead chamber in which beads required for genome extraction and amplification are accommodated also has a dual chamber structure of the outer chamber-bead chamber, so that the performance of the beads vulnerable to moisture can be maintained for a long time.

In addition, even when the bead chamber is opened, the performance of the beads is maintained by the dehumidification unit located on the upper portion of the bead chamber.

In addition, as the pre-treated extract is injected, the air remaining inside an accommodating portion is easily discharged, so that the extract having a sufficient capacity is put into the amplification module.

In addition, because the amplification module has a plurality of accommodating portions and primers and probes for amplifying different genomes are stored in each of the plurality of accommodating portions, various types of diseases can be diagnosed through single genome extraction.

In addition, the length, thickness, and patterns of a gas moving passage and an extract moving passage are provided differently depending on the location of the connected accommodating portion so that the extract or amplification product injected into the accommodating portion can be prevented from being mixed.

While the present disclosure has been particularly shown and described with reference to exemplary embodiments thereof, it will be understood by those of ordinary skill in the art that various changes in form and details may be made therein without departing from the spirit and scope of the present disclosure as defined by the following claims.

What is claimed is:

1. A specimen preparation component of a genome extraction device, comprising:
   an outer chamber, configured to receive the specimen, partitioned into a plurality of first spaces by an outer chamber partition wall; and
   an inner chamber, configured to accommodate a reagent to be used for analysis of the specimen, coupled to the outer chamber through upper openings of the plurality of first spaces and partitioned into a plurality of second spaces by an inner chamber partition wall, the inner chamber having a first position and a second position,
   wherein the inner chamber includes
   an upper inner chamber in close contact with an inner wall of the plurality of first spaces of the outer chamber,
   a lower inner chamber connected to the upper inner chamber and including a curved portion toward a radially inner side from the upper inner chamber so as to be spaced apart from the inner wall of the plurality of first spaces;
   lower openings of the plurality of second spaces of the inner chamber are covered by a second sealing member;
   a second protrusion member formed on a bottom surface of the plurality of first spaces of the outer chamber, the second position tearing open the second sealing member allowing fluid accommodated in the plurality of second spaces to be introduced into the first spaces of the outer chamber.

2. The specimen preparation component of claim 1, wherein upper openings of the plurality of second spaces of the inner chamber are covered by a first sealing member, and the genome extraction device further comprises a cover configured to cover the upper openings of the plurality of first spaces of the outer chamber and having a first protrusion member formed on a bottom surface of the cover and configured to tear the first sealing member.

3. The specimen preparation component of claim 2, wherein the first sealing member and the second sealing member are films.

4. The specimen preparation component of claim 2, wherein the first protrusion member includes:
   protrusions protruding from the bottom surface of the plurality of first spaces by a first height; and
   wing portions extending from the protrusions and protruding from the bottom surface by a second height that is lower than the first height.

5. The specimen preparation component of claim 1, wherein a coupling hook is formed on an outer surface of the upper inner chamber, and an insertion space to which the coupling hook is coupled is recessed in the inner wall of the outer chamber.

6. The specimen preparation component of claim 5, wherein a locking protrusion protrudes from the inner wall of the outer chamber toward a radially inner side on an upper side of the insertion space, and when the cover is coupled to the outer chamber, the coupling hook is inserted into the insertion space by passing through the locking protrusion.

7. The specimen preparation component of claim 6, wherein, when the cover is coupled to the outer chamber, the first protrusion member is configured to tear the first sealing member and the second protrusion member is configured to tear the second sealing member so that a fluid accommodated in the plurality of second spaces of the inner chamber is introduced into the plurality of first spaces of the outer chamber.

8. The specimen preparation component of claim 1, wherein first discharge holes are formed through the bottom surface of a part of the plurality of first spaces along a circumferential direction while being spaced apart from a central portion of the outer chamber by a first distance, and second discharge holes are formed through the bottom surface of the other part of the plurality of first spaces along the circumferential direction while being spaced apart from the central portion of the outer chamber by a second distance that is greater than the first distance.

9. The specimen preparation component of claim 8, further comprising:
   a piston including
   an upper piston having an open upper portion, a fluid accommodating portion in which fluids discharged through the first discharge holes and the second discharge holes are accommodated and which is formed therein, and holes formed in a lower portion of the upper piston to be aligned with the first discharge holes or the second discharge holes;
   a close contact portion installed to be lifted or lowered inside the fluid accommodating portion; and
   a lower piston coupled to the upper piston and having a liquid port and a filter port formed on a lower portion of the lower piston.

10. The specimen preparation component of claim 9, further comprising:
    a driving unit coupled to the lower piston by passing through a base plate, wherein the lower piston rotates by driving of the driving unit so that the liquid port or the filter port communicates with one of the plurality of first spaces.

11. The specimen preparation component of claim 10, wherein, when the close contact portion is lifted inside the fluid accommodating portion, the fluids accommodated in any one of the plurality of first spaces are inhaled into the fluid accommodating portion through the liquid port, and when the close contact portion is lowered inside the fluid accommodating portion, the fluids in the fluid accommodating portion are discharged into any one of the plurality of first spaces through the filter port.

12. The specimen preparation component of claim 11, further comprising:
    an amplification preparation module including
    an injection port coupled to the genome extraction device;
    an accommodating portion that is a space in which the fluids discharged through the injection port are accommodated;
    a gas moving passage formed on one surface of the amplification module and configured to connect the injection port to the accommodating portion; and
    an extract moving passage formed on an opposite surface to the one surface and configured to connect the injection port to the accommodating portion.

* * * * *